(12) United States Patent
Gauvrit et al.

(10) Patent No.: US 9,023,643 B2
(45) Date of Patent: May 5, 2015

(54) MEDICAMENTS AND METHODS FOR TREATING MESOTHELIOMA

(75) Inventors: Anne Gauvrit, Paris (FR); Frédéric Tangy, Les Lilas (FR); Marc Gregoire, Nantes (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 514 days.

(21) Appl. No.: 12/682,457

(22) PCT Filed: Oct. 10, 2008

(86) PCT No.: PCT/EP2008/063626
§ 371 (c)(1),
(2), (4) Date: Jul. 15, 2010

(87) PCT Pub. No.: WO2009/047331
PCT Pub. Date: Apr. 16, 2009

(65) Prior Publication Data
US 2010/0278872 A1    Nov. 4, 2010

(30) Foreign Application Priority Data

Oct. 10, 2007    (EP) ..................................... 07291232

(51) Int. Cl.
| | |
|---|---|
| *C12N 15/85* | (2006.01) |
| *C12N 5/07* | (2010.01) |
| *C12N 5/0784* | (2010.01) |
| *A61K 39/12* | (2006.01) |
| *A61K 39/00* | (2006.01) |

(52) U.S. Cl.
CPC ......... *A61K 39/12* (2013.01); *A61K 2039/5154* (2013.01); *A61K 2039/5254* (2013.01); *C12N 2760/18432* (2013.01); *A61K 2039/585* (2013.01); *C12N 2760/18434* (2013.01)

(58) Field of Classification Search
None
See application file for complete search history.

(56) References Cited

U.S. PATENT DOCUMENTS 7,118,740 B1 * 10/2006 Russell et al. ................ 424/93.6

FOREIGN PATENT DOCUMENTS

| WO | 02/23994 | 3/2002 |
|---|---|---|
| WO | 2009/047331 | 4/2009 |

OTHER PUBLICATIONS

Zhu et al. Targeting Mesothelioma Using an Infectivity Enhanced Survivin-Conditionally Replicative Adenoviruses. Journal of Thoracic Oncology: Sep. 2006—vol. 1—Issue 7—pp. 701-711.*
Bramwell, V.W. et al., "The rational design of vaccines," DDT Drug Discovery Today (2005) 10(22):1527-1534.
Ebstein, F. et al., "Cytotoxic T cell responses against mesothelioma by apoptotic cell-pulsed dendritic cells," Am. J. Resp. Critical Care Med. (2004) 169(12):1322-1330.
Gauvrit, A. et al., "Measles virus induces oncolysis of mesothelioma cells and allows dendritic cells to cross-prime tumor-specific CD8 response," Cancer Res. (2008) 68(12):4882-4892.
Gregoire, M. et al., "Anti-cancer therapy using dendritic cells and apoptotic tumour cells: pre-clinical data in human mesothelioma and acute myeloid leukaemia," Vaccine (2003) 21(7-8):791-794.
Gregoire, M. et al., "Immunotherapy and malignant mesothelioma: clinical perspectives," Bulletin du Cancer (2007) 94(1):23-31.
McDonald, C.J. et al., "A measles virus vaccine strain derivative as a novel oncolytic agent against breast cancer," Breast Cancer Research and Treatment (2006) 99(2):177-184.
Peng, K.W. et al., "Oncolytic measles virotherapy for ovarian cancer," Cancer Gene Therapy (2004) 11(12):846.
Peng, K.W. et al., "Intraperitoneal therapy of ovarian cancer using an engineered measles virus," Cancer Res. (2002) 62(16):4656-4662.
Vidal, L. et al., "Reovirus and other oncolytic viruses for the targeted treatment of cancer," Targeted Oncology (2006)1(3):130-150.
International Search Report and Written Opinino for Application No. PCT/EP2008/063626 dated Jan. 13, 2009 (17 pages).
Aldjandhami, I. et al., Attenuated measles virus as a therapy for thoracic malignancies. Poster contribution TP112 at Thoracic Society of Australia and New Zealand Annual Spring Meeting 2007, Respirology (2007) 12, Suppl. I: A30-A78.
Hegmans et al., Immunotherapy of murine malignant mesothelioma using tumor lysatepulsed dendritic cells, Cancer Research, May 15, 2005, 171(10):1168-1177.
Hilleman et al., Development and evaluation of the Moraten measle virus vaccine, JAMA, 1968, 206(3): 587-590.

* cited by examiner

*Primary Examiner* — Michelle S Horning
(74) *Attorney, Agent, or Firm* — Michael Best & Friedrich LLP

(57) ABSTRACT

The present invention relates to the use of at least one attenuated measles virus for the manufacture of a medicament intended for treating malignant mesothelioma in an individual.

11 Claims, 6 Drawing Sheets

MEDICAMENTS AND METHODS FOR TREATING MESOTHELIOMA

CROSS-REFERENCE TO RELATED APPLICATIONS

Figure 1:
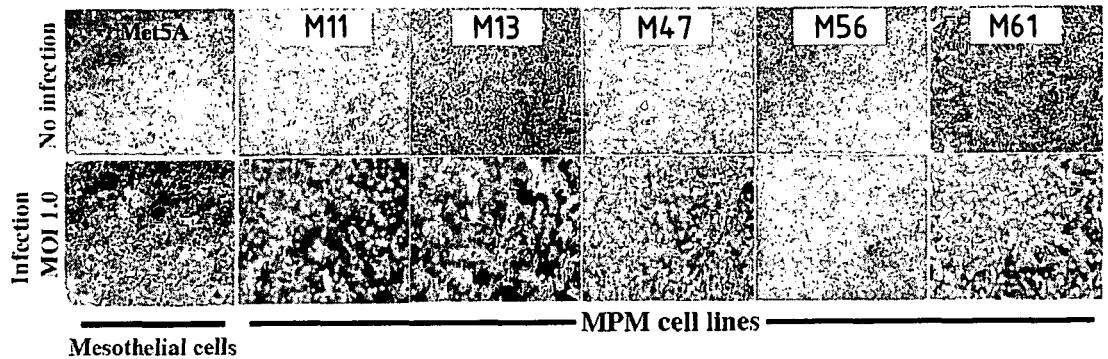

This patent application is a national stage filing under 35 U.S.C. 371 of International Application No. PCT/EP2008/063626, filed Oct. 10, 2008, which claims priority to European Patent Application No. 07291232.2, filed Oct. 10, 2007, the disclosures of each of which are incorporated by reference herein in their entirety for any purpose. Priority to each application is hereby claimed.

FIELD OF THE INVENTION

The present invention relates to methods and medicaments intended to cure cancers, such as malignant mesothelioma.

BACKGROUND OF THE INVENTION

Malignant mesothelioma (MM) are relatively rare and highly aggressive neoplasms, arising from the uncontrolled proliferation of mesothelial cells lining serosal cavities, most commonly the pleura (Malignant Pleural Mesothelioma or MPM) (Robinson et al. (2005) *Lancet* 366:397-408). Epidemiologic studies have established that exposure to asbestos is one of the most important MPM etiologic factor in industrialized countries (Gruber (2005) *Lung Cancer* 49S1:S21-S23; Bartrip (2004) *Postgrad Med. J.* 80:72-76). Although worldwide usage of asbestos has been considerably reduced, the incidence of mesothelioma is expected to rise in the next two decades, because of a long latency period (20 to 40 years) between asbestos exposure time and clinical symptoms apparition.

Today, cancer diagnosis is usually established at an advanced stage because of the absence of overt symptoms in the early period of the disease, thus making poor the prognosis for mesothelioma patients. Consequently, MPM is actually considered as a cancer relatively refractory to all conventional treatment modalities. Accordingly, there is a pressing need for the development of new therapeutic approach.

During the past decade, there has been an increasing interest in virotherapy, partly related to the growing knowledge in the production of recombinant viral vectors for human gene therapy. Numerous RNA replicating viruses are now considered as potential cancer therapeutics. As such, therapy of MPM using engineered replication-competent Herpex Simplex Viruses (HSV) has been proposed, based on in vitro studies and results obtained on a murine model of MPM (Adusumilli et al. (2006) *J. Gene Med.* 8:603-615). However, the long term safety of these engineered viral vectors in humans is not known and extensive clinical trials will be necessary to document this aspect of HSV usage.

Accordingly, there is a need for viral vectors with recognized safety liable to be used in the frame of mesothelioma treatment.

MV (Measles Virus) is an enveloped, negative single strand RNA virus belonging to the Paramyxoviridae family, genus *Morbilli* virus. Various replication-competent live attenuated strains of MV have been developed for producing vaccines against measles. By way of example, Schwartz, Moraten, or Zagreb (which are derived from MV samples isolated from an Edmonston patient) are safe and well-documented MV vaccine strains.

It has been shown recently that in vivo administration of a replication-competent Edmonston MV strain resulted in growth slowing or sometimes regression of tumors established animal models of lymphoma and myeloma cancer (Grote et al. (2001) *Blood* 97:3746-3754; Peng et al. (2001) *Blood* 98:2002-2007). Besides, Anderson et al. (2004) *Cancer Res.* 64:4919-4926, have shown in in vitro experiments that high CD46 expression by tumor cells was necessary for the infection and the killing of these cells by a live attenuated Edmonston MV strain. However, it is known that CD46 is variably expressed by human carcinomas (Niehans et al. (1996) *American J. Pathol.* 149:129-142), thereby casting doubts on the general applicability of live attenuated MV strains for treating cancers.

SUMMARY OF THE INVENTION

The present invention arises from the unexpected finding, by the present inventors, that attenuated measles virus could efficiently infect and kill mesothelioma cells. Furthermore, the present inventors have shown that dendritic cells contacted with lysate from attenuated measles virus-infected mesothelioma cells could activate anti-mesothelioma CD8 T cells.

Thus, the present invention relates to an attenuated measles virus for use in the treatment of malignant mesothelioma in an individual.

The present invention also relates to the use of at least one attenuated measles virus for the manufacture of a medicament intended for treating malignant mesothelioma in an individual.

The present invention also relates to a method for treating malignant mesothelioma in an individual, wherein a therapeutically effective quantity of at least one attenuated measles virus is administered to said individual.

The present invention further relates to a method for preparing vaccinal dendritic cells intended for treating cancer in an individual, comprising the following steps:

in vitro infection of cancer cells, preferably taken from the individual, by an attenuated measles strain to yield a cell lysate;

contacting dendritic cells with the cell lysate to yield vaccinal dendritic cells.

The present invention also relates to vaccinal dendritic cells liable to be obtained by the above-defined method of preparation, to a pharmaceutical composition comprising said vaccinal dendritic cells as active ingredient, in association with a pharmaceutically acceptable carrier, to said vaccinal dendritic cells for use in the treatment of cancer in an individual, and to the use of said vaccinal dendritic cells, for the manufacture of a medicament intended for treating cancer in an individual.

The present invention further relates to a method for treating cancer in an individual, wherein a therapeutically effective quantity of vaccinal dendritic cells liable to be obtained by the above-defined method of preparation are administered to said individual.

DETAILED DESCRIPTION OF THE INVENTION

As intended herein, the individual is preferably a mammal, more preferably a human. Preferably also, the individual has been exposed to asbestos.

As intended herein, the expression "attenuated measles virus" designates any virus derived from a measles-causative virus and presenting a decreased virulence with respect to said measles-causative virus. As intended herein the attenuated measles virus can be derived from measles-causative virus by any technique known to the man skilled in the art, such as serial passages on cultured cells and/or genetic engineering. In particular, the attenuated measles virus may be a recombinant virus, optionally expressing additional genes. More particularly, the attenuated measles virus may be a measles virus wherein the expression of one or more proteins, preferably the accessory C protein, is abolished. It is preferred that the attenuated measles virus causes essentially no measles symptoms when administered to a human. Besides, the attenuated measles virus is preferably alive and replication-competent.

Preferably, the attenuated measles virus is an Edmonston strain. Edmonston strains of attenuated measles virus are well-known to one of skill in the art and are notably described in Griffin (2001)*Field's Virology* 4th Edition vol. 2 Knipe and Howley (ed.) Lippincott-Raven Publishers, Philadelphia, 1401-1441; Hilleman (2002) *Vaccine* 20:651-665). More preferably, the attenuated measles virus is selected from the group constituted of a Schwartz strain and a Moraten strain. These strains, which genomes have been shown to be identical, are well-known to the man skilled in the art and are widely used for the production of vaccines against measles. They are notably described in Schwarz (1962) *Am. J. Dis. Child* 103:216-219; Parks et al. (2001) *J. Virol.* 75:921-933 and Parks et al. (2001) *J. Virol.* 75:910-920. Most preferably, the attenuated measles virus is produced from the pTM-MVSchw plasmid (SEQ ID NO: 1) described by Combredet et al. (2003) *J. Virol.* 77:11546-11554.

Cancers to be treated within the frame of the present invention are preferably malignant mesotheliomas, more preferably malignant pleural mesotheliomas or peritoneal mesotheliomas, most preferably malignant pleural mesotheliomas. Such cancers are notably described in Kazan-Allen (2005) *Lung cancer* 49S1:S3-S8 and Robinson et al. (2005) *Lancet* 366:397-408.

Where the attenuated measles virus is administered to an individual, it can be administered through the intrapleural cavity or by the intranasal, intramuscular, intravenous or subcutaneous routes. Where the attenuated measles virus is administered through the intrapleural cavity, it is preferably administered in close proximity or directly into the tumors to be treated. If necessary, the attenuated measles virus can be associated to any suitable pharmaceutically acceptable carriers. The therapeutically effective quantity of attenuated measles virus to be administered is preferably in the range of from $10^3$ to $10^6$ 50% tissue culture infective doses (TCID50). TCID50 determination is well known to one of skill in the art and is notably described by Karber (1931) *Arch. Exp. Path. Pharmak.* 162:840-483.

The step of taking the cancer cells from the individual to be treated by the vaccinal dendritic cells is preferably not included in the above-defined method of preparation of vaccinal dendritic cells. This step can proceed according to any technique known to one of skill in the art for taking cells, such as biopsies and effusions (e.g. pleural effusions). After being taken, the cancer cells can be maintained in culture according to classical techniques, or frozen (e.g. at −80° C.) for conservation, for instance. Where the cancer cells do not originate from the individual to be treated by the vaccinal dendritic cells, they can notably derive from allogenic human mesothelioma cell lines.

In the above-defined method of preparation, infection of the cancer cells by the attenuated measles virus can proceed by directly contacting cells and virus, for instance at a Mutliplicity Of Infection (MOI) of 1, with an incubation of 2 hours at 37° C. After infection, death of the infected cells proceeds spontaneously due to virus action. A syncitia is usually first formed followed by lysis of the cells. This phenomenon can be evidenced by direct microscopic observation of infected cells. As intended herein "cell lysate" encompasses both whole (or total) cell lysate, or fractions of the cell lysate, such as membrane fractions (e.g. cytoplasmic inclusion bodies or apobodies). As will be well-understood by those skilled in the art, the cell lysate obtained in the first step of the above-defined method of preparation corresponds to a virus infected cancer cell lysate.

Dendritic cells can be obtained by numerous ways well known to the man skilled in the art. The dendritic cells preferably originate from the individual to be treated. It is presently preferred that the dendritic cells are monocyte-derived dendritic cells. The obtention of monocyte-derived cells is particularly well known to one of skill in the art. Preferably, monocyte-derived cells can be obtained following the general methodology described in Example 4 or by Spisek et al. (2001) *Cancer Immunology Immunotherapy* 50:417-427, or by Royer et al. (2006) *Scand. J. Immunol.* 63:401-409. Where the monocyte-derived dendritic cells originate from the individual to be treated, monocytes can be obtained from leukapheresis of said individual.

As will be apparent to one skilled in the art, contacting of the dendritic cells and of the cell lysate should be maintained for a time sufficient to enable an effective loading of the dendritic cells by antigens present in the cell lysate. Once loaded (or pulsed), vaccinal dendritic cells according to the invention are obtained. Loading can proceed by following the general methodology described in Example 4. An exemplary contact period between dendritic cells and the cell lysate sufficient to enable efficient loading of the dendritic cells is of about 24 hours. In particular, the contact period can be maintained until the dendritic cells are in an activated state. The activated state is usually reached after the dendritic cells have been loaded. The activated state (or mature state) of dendritic cells can be evidenced by numerous markers well known to one of skill in the art, such as membrane or cytokine markers. Such markers of activated dendritic cells are notably listed in Example 5.

Thus, vaccinal dendritic cells obtainable according to the method of preparation of the invention are particularly advantageous since they are potent stimulators of anti-cancer CD8 T cells. Equally advantageous, the method of preparation according to the invention allows the preparation of vaccinal dendritic cells in an activated state.

BRIEF DESCRIPTION OF THE FIGURES

FIGS. 1, 2, 3, 4 and 5: Mesothelioma susceptibility to attenuated Measles Virus (MV).

FIG. 1—Selective Oncolytic activity of Schwarz MV vaccine strain. A panel of human epithelioid mesothelioma cell lines (M11, M13, M47, M56 & M61) and an immortalized normal mesothelial cell line (Met5A) were infected with non-recombinant MV (MOI 1.0) and microscope observations of infected cultures morphology were performed 72 hours later.

FIGS. 2-3—Higher surface expression level of CD46 receptors for tumoral cells in comparison with their normal counterparts. Cells were stained with FITC-conjugated CD46-specific antibodies (grey histogram) or related isotype Ig control (white histogram) (FIG. 2). Numbers indicate the mean fluorescence index and histogram shows mean values of CD46 expression obtained for mesothelial (white bar) and mesothelioma (hatched bar) cell lines (FIG. 3).

Figure 4:
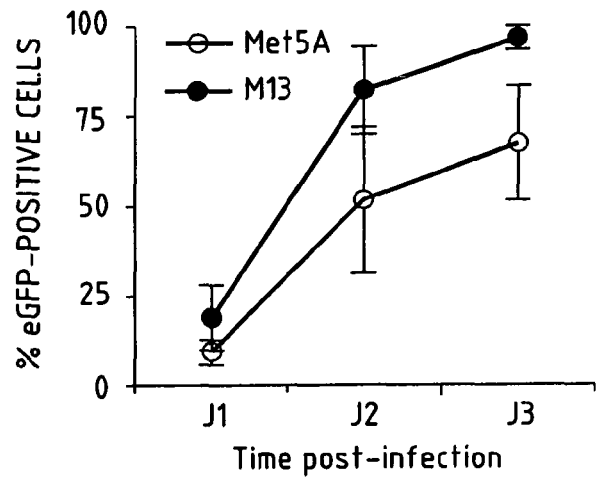
Figure 5:
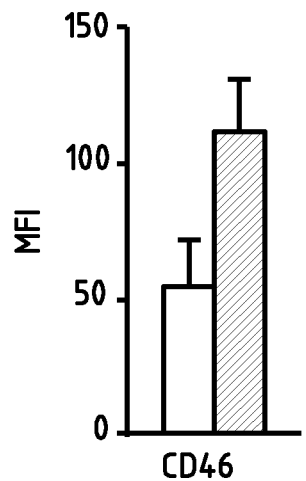

FIGS. 4-5—Schwarz MV vaccine strain preferentially infects transformed tumoral cells. Equal numbers of M13 and Met5A cells were cultured separately (FIG. 4) or co-cultured (FIG. 5) overnight, allowing cellular adherence, and infection was done at MOI of 1.0 with eGFP-recombinant MV. In separate cultures, analysis of eGFP expression was performed at different times post-infection (24, 48, & 72 hours) by flow cytometry (FIG. 4). In co-culture model, the same experiment was conducted along with HLA-A2 staining, as HLA alleles differential expression allowed distinction between two cell lines. Histogram shows % eGFP-positive cells for Met5A (white bar) and M13 (black bar) cells from co-culture (FIG. 5).

Figure 6:
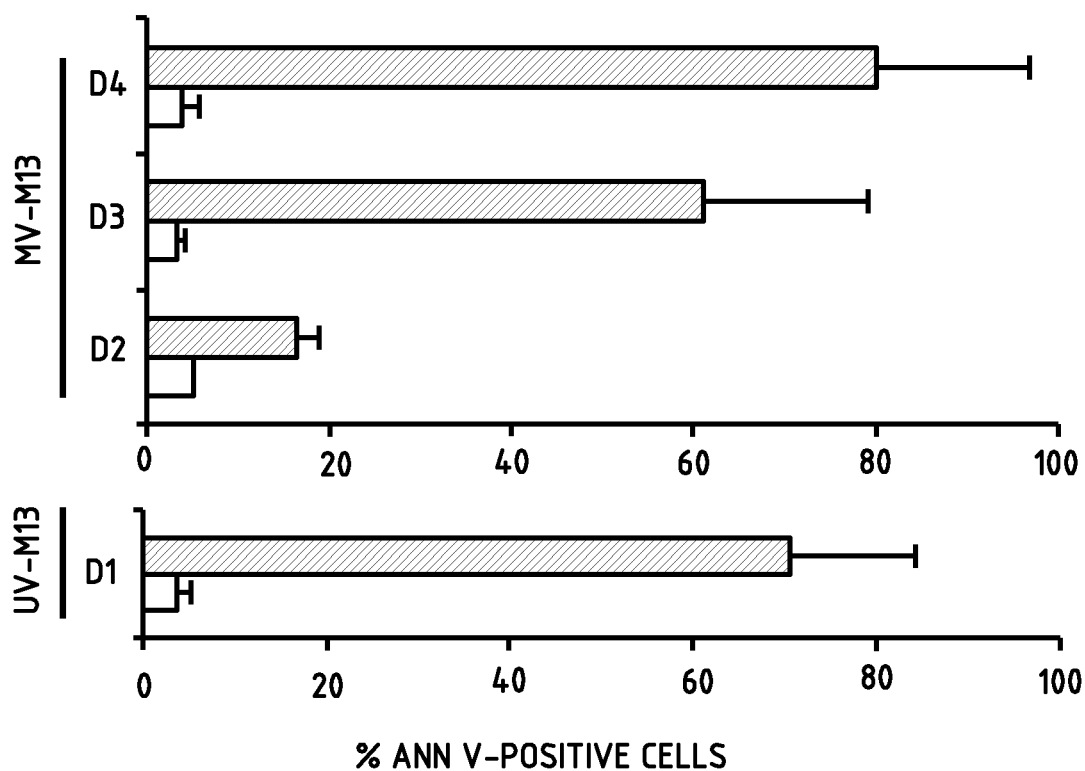

FIG. 6: Immunogenicity of MV-infected mesothelioma cell line.

FIG. 6—Cellular death induced by MV- and UV-treatments. Flow cytometry analysis of M13 tumoral cells apoptosis triggered by UV exposure (5 kJ/cm$^2$) or MV infection (MOI=1.0) at the indicated time points (D1=24 h, D2=48 h, D3=72 h, and D4=96 h) (hatched bars) vs. untreated control cells (white bars).

Figure 7:
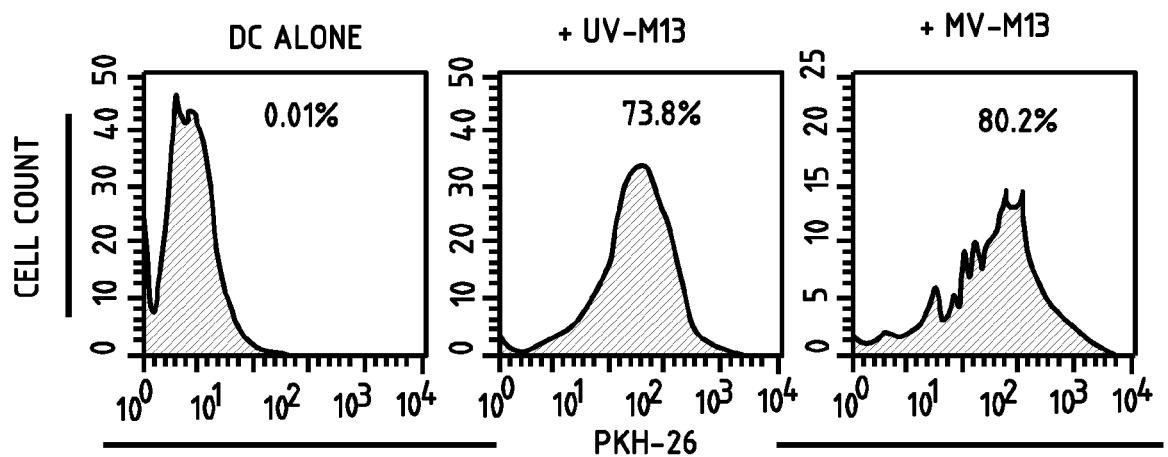
Figure 8:
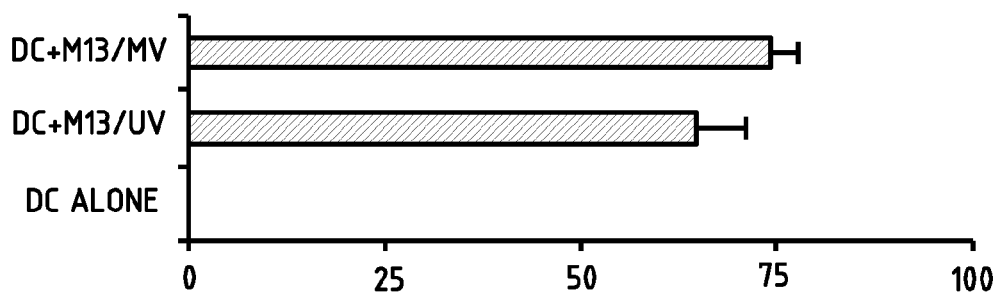

FIGS. 7 and 8: Phagocytosis of apobodies by monocyte-derived DCs.

FIG. 7—UV- or MV-treated M13 tumor cells were labelled with PKH-26 and co-cultured with immature DCs for 24 hours. Harvested DCs were subsequently stained with FITC-conjugated anti HLA-DR antibodies and analysed by flow cytometry. One representative experiment of three with similar results is shown. The number of double-positive DCs, that is the percentage of PKH-26 positive DCs gated on basis of HLA-DR expression (FITC-conjugated antibodies, clone B8.12.2, Immunotech), indicates the phagocytosis efficiency of apoptotic cells.

FIG. 8—The histogram represents mean values of phagocytosis yield obtained for each loading condition tested.

Figure 9:
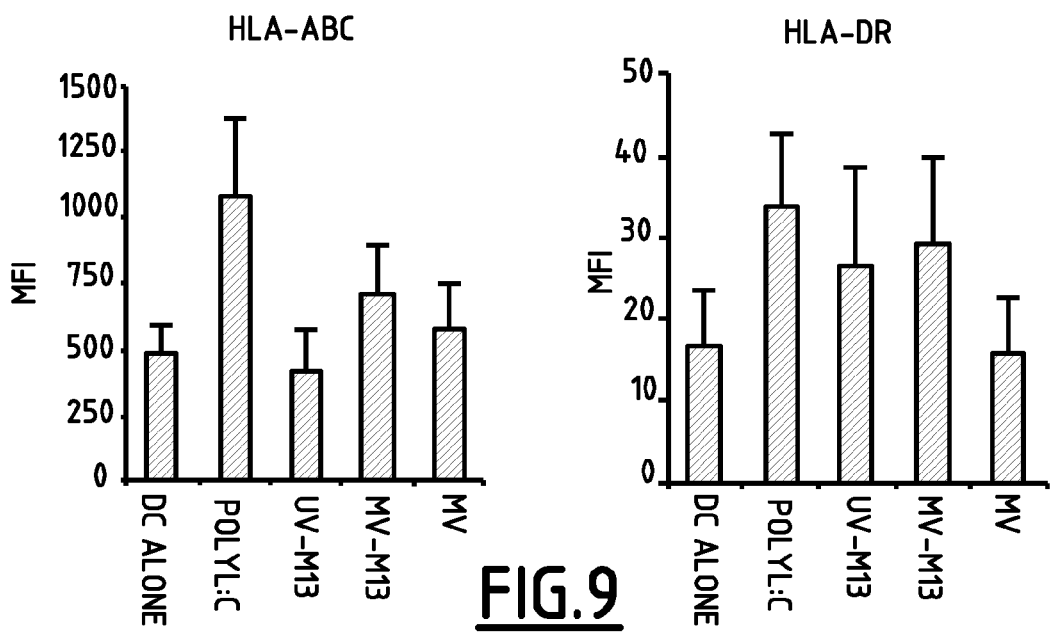
Figure 10:
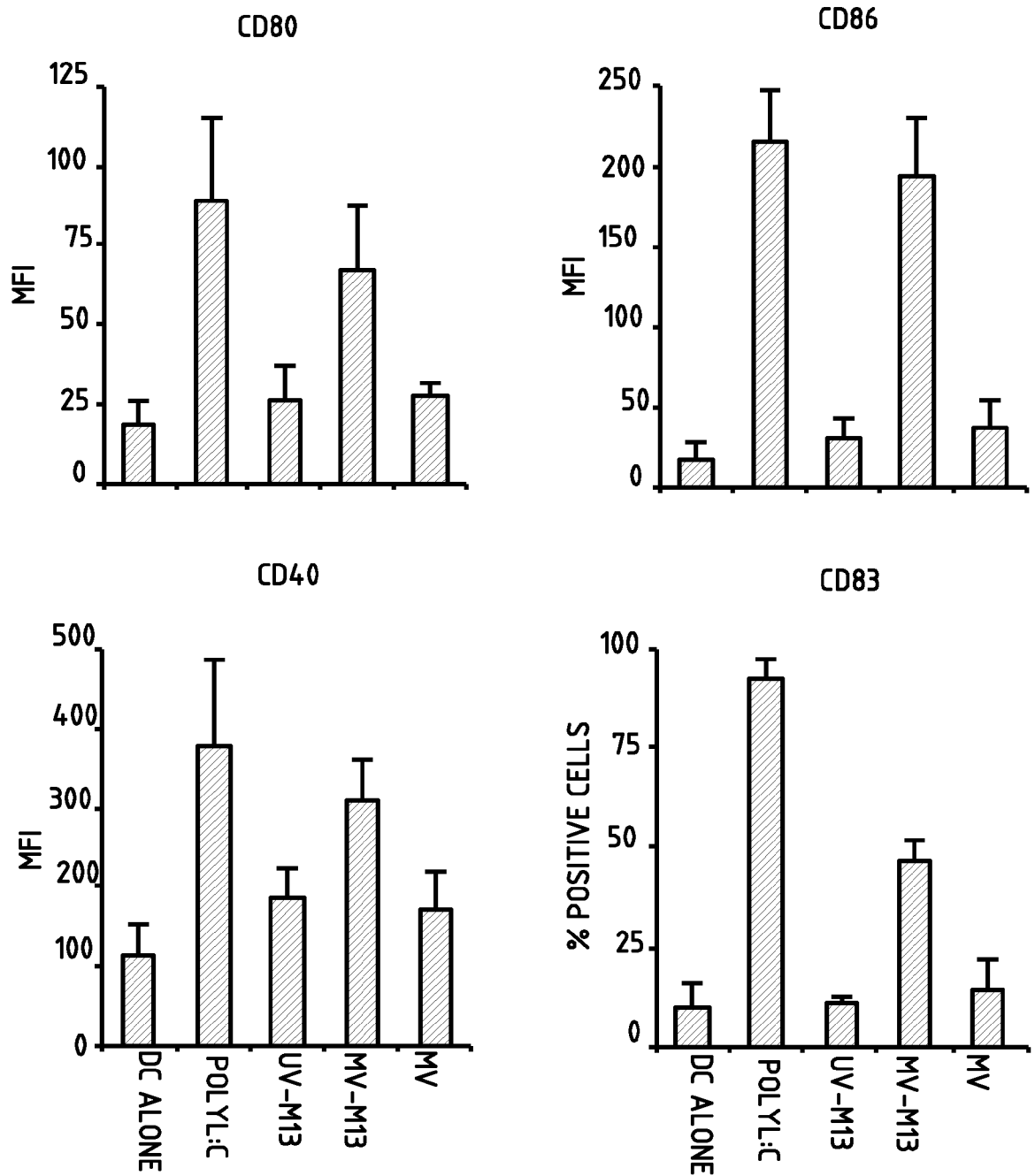
Figure 11:
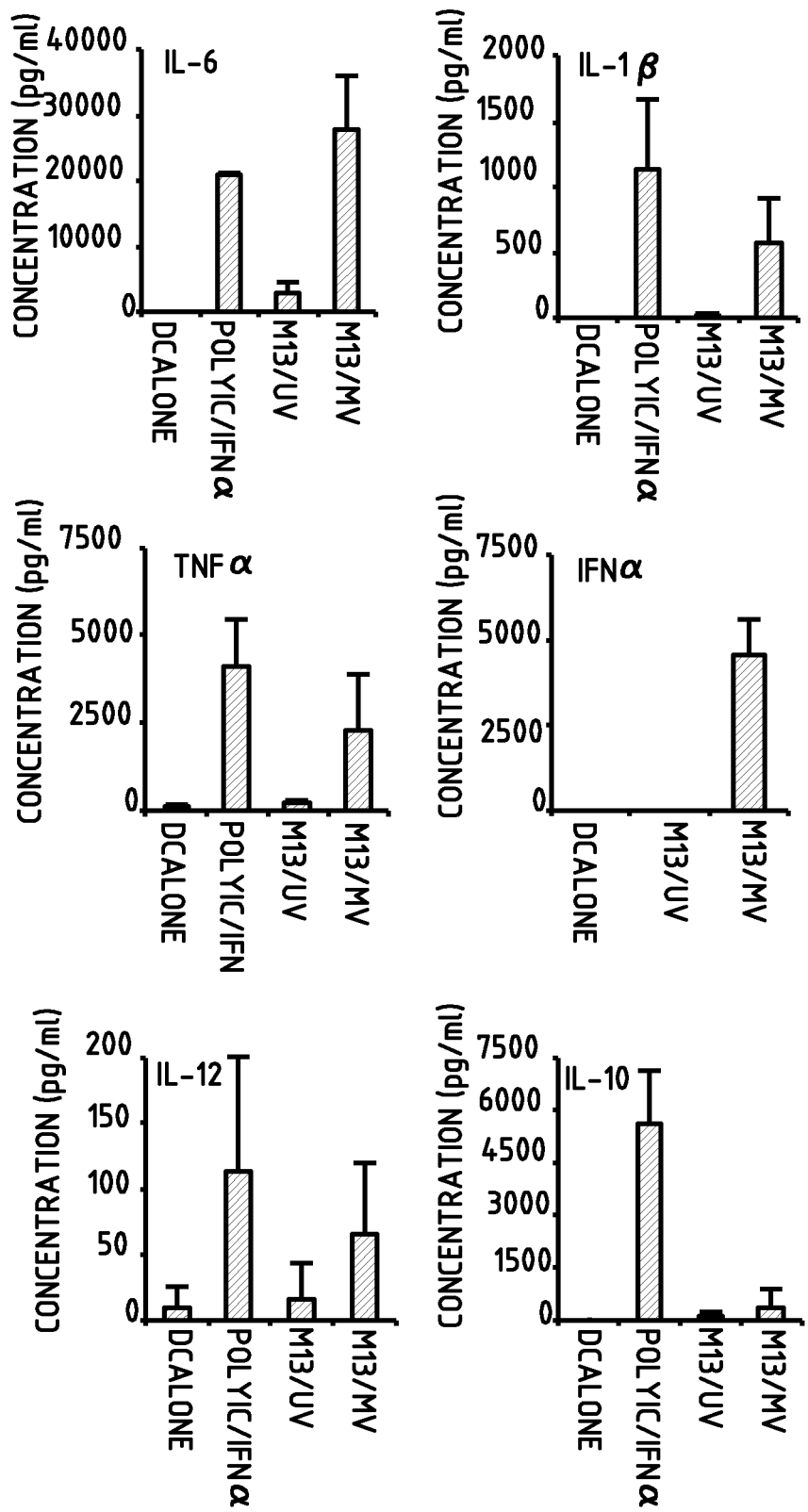

FIGS. 9, 10 and 11: DC maturation induced by co-culture with MV-infected mesothelioma cells.

FIGS. 9 and 10—Immature DCs and M13 tumoral cells were cultured in the indicated combinations (ratio 1/1) for 24 hours. As controls, DCs were incubated with TLR3 ligand, polyinosinic:polycytidylic acid (50 µg/ml; Sigma), or directly infected with MV (MOI=1.0). Subsequently DCs were harvested and stained with a PE-conjugated antibody panel specific for the indicated cell surface molecules (FIG. 9—HLA molecules; FIG. 10—Maturation Markers). DCs were gated according to their morphology characteristic, and dead cells were excluded on basis of TOPRO-3 staining (Molecular Probes). DCs surface phenotype was analysed by three-colors flow cytometry. Histogram shows means values obtained from four independent donors.

FIG. 11—DC cytokine secretion pattern was investigated on 24 hours supernatant co-culture by CBA (for IL-6, IL-1β, TNFα, IL-12 & IL-10) and ELISA (for IFNα) assays.

Figure 12:
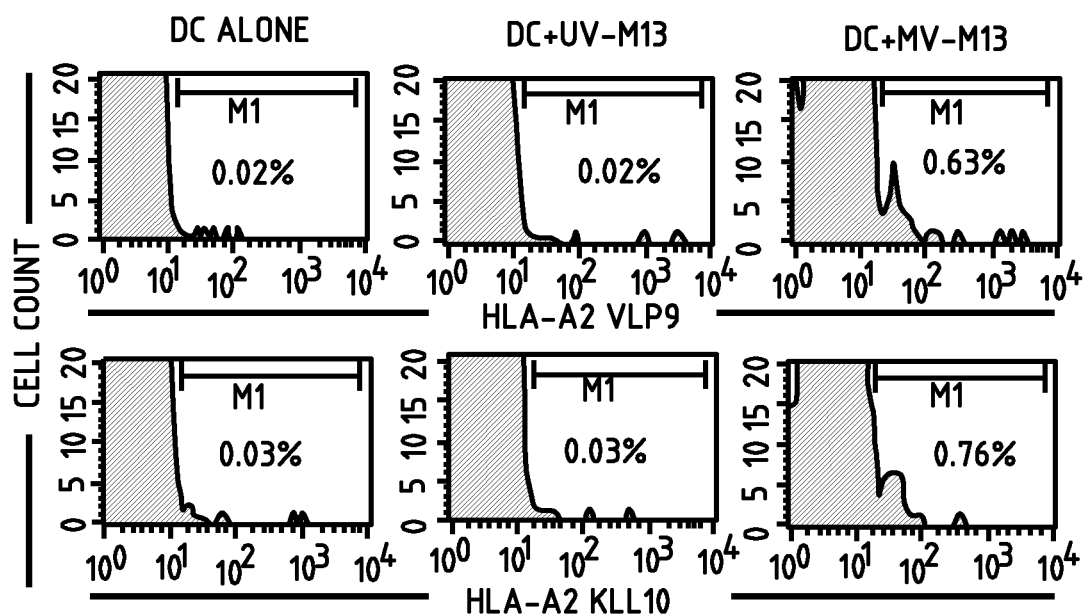

FIG. 12: DCs loaded with MV-infected mesothelioma cells induce MSLN-specific CD8 T cell priming.

FIG. 12—Number of MSLN-specific CD8 T cells, derived from one week sensitization co-culture with unpulsed or UV-M13 or MV-M13 pulsed DCs, was analysed by flow cytometry. Histogram indicates the percentage of PE-tetramer positive cells among T cells gated on basis of human CD8 expression (PE-Cy5-conjugated antibodies, clone RPA-T8, BD Biosciences). One representative experiment is shown.

EXAMPLES

Example 1

Mesothelioma Susceptibility to MV Infection and Oncolytic Activity

To compare MV-related cytopathic effect on tumoral and non-tumoral cells, a panel of five epithelioid mesothelioma cell lines (M11, M13, M47, M56, and M61) and mesothelial cells (Met5A) were infected with a Schwarz vaccine strain at a Multiplicity Of Infection (MOI) of 1.0.

The mesothelioma cell lines (M11, M13, M47, M56, and M61) were established from pleural effusion collected by thoracocentesis of cancer patients. Diagnosis of epithelioid mesothelioma was established by biopsies immunohistochemical staining. The control mesothelial cell line (Met5A) was isolated from pleural fluids of cancer-free patients and immortalized by transfection with the pRSV plasmid encoding SV40 T-antigen (ATCC-LGC Promochem, Molsheim, France). Cell lines were maintained in RPMI-1640 medium supplemented with 10% heat-inactivated Foetal Calf Serum (FCS from Biowest, Nuaille, France), 1% L-glutamine and 1% penicillin/streptomycin antibiotics (all purchased from Sigma, St Quentin Fallavier, France). Cellular cultures were routinely checked for *Mycoplasma* contaminations using Hoechst 33258 staining (Sigma).

Attenuated MV Schwarz vaccine strains were obtained from F. Tangy (Pasteur Institut, France). Schwarz MV was rescued from the pTM-MVSchw (SEQ ID NO: 1) cDNA by use of the helper-cell-based rescue system described by Radecke et al. (1995) *EMBO J.* 14:5773-5784 and modified by Parks et al. (1999) *J. Virol.* 73:3560-3566. Briefly, 293-3-46 helper cells were transfected with 5 µg of pTM-MVSchw and 0.02 µg of pEMC-Lschw expressing the Schwarz MV-L gene (Combredet et al. (2003) *J. Virol.* 77:11546-11554) (SEQ ID NO: 2). After overnight incubation at 37° C., a heat shock was applied for 2 h at 43° C., and transfected cells were transferred onto a Vero cell monolayer. Syncytia that appeared in 15 days coculture were transferred to 35-mm wells and then expanded in 75-cm$^2$ and 150-cm$^2$ flasks of Vero cells culture in 5% FCS DMEM. When syncytia reached 80-90% confluence, the cells were scraped into a small volume of OptiMEM and frozen-thawed once. After low-speed centrifugation to pellet cellular debris, virus-containing supernatant was stored at −80° C. The titer of recombinant MV stock was determined by an endpoint limit-dilution assay on Vero cells. The TCID50 was calculated by use of Kärber method (Karber (1931) *Arch. Exp. Path. Pharmak.* 162:480-483).

Viral infections of the mesothelioma cell lines were performed at a MOI=1.0 for 2 hours incubation at 37° C. Three days following MV infection, typical morphological modifications of MV-infected cells were observed, that is development of an important cytopathic effect (CPE) on most tumoral MPM lines (4/5), by contrast with non cancerous Met5A cells (FIG. 1). CPE was evidenced through development of more or less important syncitia, which finally led to shedding in culture supernatant of cytoplasmic inclusion bodies of dead tumoral cells (FIG. 1). The development of these multinucleated giant syncitia is characteristic of measles infection and is produced by fusion of HA$^+$ infected cells with neighbour CD46$^+$ culture cells.

Figure 2:
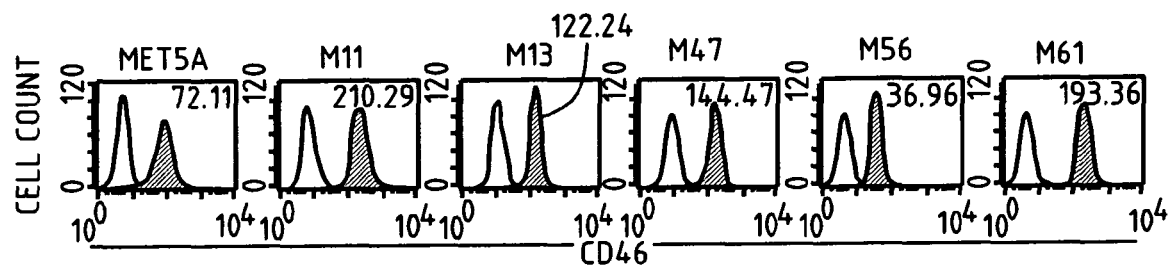
Figure 3:
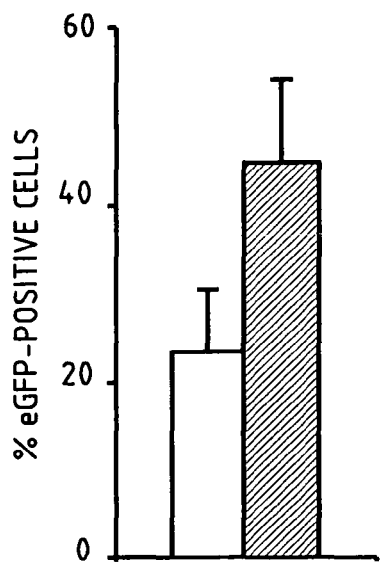

A significant upregulated expression of live-attenuated MV strains receptor CD46 by mesothelioma cells could be evidenced (FIGS. 2-3).

In order to quantify susceptibility to MV infection, Met5A and M13 cell lines were infected with eGFP-recombinant MV stock (Combredet et al. (2003) *J. Virol.* 77:11546-11554). The GFP-transgene expression was used as a marker of viral infection, thus allowing determination of infected cells percentage by flow cytometry. MV infection yield of both culture cells was dose-dependent (MOI ranging from 0.01 to 5.0), indicating the specificity of eGFP signal. Whereas Met5A was infected by the MV strain (for MOI ranging from 0.5), M13 was also significantly infected by MV, but always at lowest MOI (for MOI ranging from 0.1). A significant increased infection yield of tumour cells in comparison to normal cells (for MOI 1.0), was also observed both in cellular separate culture (FIG. 4) and co-culture (FIG. 5) systems (ratio 1:3) at 48 hours post-infection. Moreover, virus infection could also be evidenced by down-regulation of CD46 surface expression observed in infected cellular cultures.

Thus, according to these in vitro results, mesothelioma tumors present a more important susceptibility both to MV-mediated infection and MV-related cytolytic activity than mesothelial tissue. Consequently, MPM appears as a relevant candidate for virotherapy approach based on measles virus administration.

Example 2

Tumoral Cell-Death Induced by MV and UV Treatments

After demonstrating that MV is able to infect mesothelioma cells, the inventors verified if virus infection could also lead to apoptosis-mediated cell death.

Sub-confluent monolayer M13 cells culture were either MV-infected (MOI 1.0), or UV-B-irradiated (312 nm-5 kJ/m$^2$) using an UV Stratalinker2400 (Stratagene Europe, Amsterdam, Netherlands), as positive control for apoptosis. Cells were collected at different times post-treatment, and cellular death was quantified as described by Ebstein et al. (2004) *Am. J. Respir. Crit. Care Med.* 169:1322-1330 by concomitant phosphatidylserine and Annexin-V stainings.

As shown in FIG. 6, 24 hours exposition of M13 cells to UV-B irradiation and 72 hours infection of M13 cells with MV yielded an equivalent rate of tumoral cell death (comprised between 70% and 80% of Annexin-V positive cells), which indicates that MV induces apoptosis in infected tumor cells. The thus-defined M13 cell death-induced conditions were used in following experiments.

Moreover, virus-related cell killing was also confirmed by observation of an important cytopathic effect, leading to complete dislocation of M13 cellular layer 72-96 hours post-infection (FIG. 1).

Example 3

Follow-Up of Viral Replication Cycle in MV-Infected Tumoral Cells

In order to follow viral growth kinetic in infected M13 cells culture (MOI=1.0), RT-PCR specific for viral dsRNA potential receptors (Mda-5, TLR-3, RIG-I and PKR) were performed. Specific primers for the β-actin gene were used as an internal experiment control.

Briefly, M13 cells were either incubated with polyinosinic:polycytidylic acid ligand (10 µg/ml) or MV (MOI=1.0) and cellular pellets were collected at different times. Whole cellular RNA was then extracted using RNeasy kits (Qiagen, Courtaboeuf, France) according to manufacturer's instructions, and reverse-transcribed using RTase (Invitrogen, Paisley, UK). Resulting cDNA was used as template for PCR amplification using primers specific for Mda-5, TLR-3, RIG-I, PKR, IFNβ, and β-actin. PCR primers sequences are listed in Table 1. PCR products were visualized by agarose gel electrophoresis.

TABLE 2 primer sequences

| Primer | | Sequence | Fragment size (bp) | SEQ ID NO: |
|---|---|---|---|---|
| β-actin | Forward | ATCTGGCACCACACCTTCTACAATGAGCTGCG | 837 | 3 |
|  | Reverse | CGTCATACTCCTGCTTGCTGATCCACATCTGC |  | 4 |
| TLR-3 | Forward | ATTGGGTCTGGGAACATTTCTCTTC | 319 | 5 |
|  | Reverse | GTGAGATTTAAACATTCCTCTTCGG |  | 6 |
| Mda-5 | Forward | GAGCAACTTCTTTCAACCAC | 633 | 7 |
|  | Reverse | GAACACCAGCATCTTCTCCA |  | 8 |
| RIG-I | Forward | GAACGATTCCATCACTATCC | 580 | 9 |
|  | Reverse | GGCATCATTATATTTCCGCA |  | 10 |
| PKR | Forward | CTTCTCAGCAGATACATCAG | 689 | 11 |
|  | Reverse | GTTACAAGTCCAAAGTCTCC |  | 12 |

It could thus be shown that a viral replication peak occurred between 1 day to 4 days post-infection of mesothelioma M13 cells. Besides, PCR products corresponding to viral dsRNA potential receptors (Mda-5, TLR-3, RIG-I and PKR) could also be evidenced.

Example 4

Efficient Uptake of Apoptotic Mesothelioma Cells by Immature DCs

The uptake by dendritic cells (DCs) of apobodies from MV-infected (72-hours) was then studied and compared to that of UV-irradiated (24-hours) M13 tumoral cells.

Dendritic cells were derived from monocytes generated from leukapheresis harvests of HLA-A0201 healthy donors (EFS, Nantes, France), after obtaining informed consent. Monocytes-enriched fraction (>85% purity) was first separated by Ficoll density gradient centrifugation (PAA Laboratories, Les Mureaux, France). Monocytes were then enriched by elutriation (counterflow centrifugation) using a Beckman Avanti J20 centrifuge equipped with a JE5.0 rotor and a 40-ml elutriation chamber. Routinely, purity of elutriated monocytes was over 80%, as assessed by flow cytometry based on the detection of the CD14 marker. Monocytes were cultured at $2 \times 10^8$ cells/ml with 500 IU/ml GM-CSF and 200 IU/ml IL-4 (Cell Genix Technology, Freiburg, Germany). Cells were then allowed to differentiate for 6 days.

On day 6, monocytes-derived DCs were collected from culture supernatant and seeded in culture for subsequent loading. Immature DCs were incubated with $2 \cdot 10^8$ cells/ml of apoptotic material, derived from UV-treated or MV-infected allogenic M13 tumoral cells, for additionally 24 hours co-culture (ratio 1:1). DC phagocytosis yield analysis was assessed both by flow cytometry and confocal laser microscopy, as previously described (Massé et al. (2002) *Cancer Research* 32:1050-1056). Briefly, UV- or MV-treated M13 cells were labelled with PKH-26 membrane dye colorant, according to the manufacturer's protocol (Sigma, St Quentin Fallavier, France). After 24 hours co-culture, DCs were stained with FITC-conjugated anti HLA-DR antibodies (Immunotech, Marseilles, France). After PBS washes, cells were harvested and analysed either on a FACSCalibur (BD Biosciences, Grenoble, France), or with a TCS NT microscope (Leica Instruments, Heidelberg, Germany). DCs that have ingested apoptotic cells were identified as HLA-DR/PKH-26 double positive cells (FIG. 7).

As shown in FIG. 8, it could be evidenced that DCs efficiently engulfed UV- and MV-treated mesothelioma cells at the same rate, as illustrated by a similar percentage of PKH26-positive DCs gated on basis of HLA-DR expression (65% and 74% for DCs loaded respectively with UV- or MV-treated M13 cells).

Confocal laser-scanning microcopy experiments further confirmed an efficient internalization of apoptotic M13 cells by immature DCs within 24 hours co-culture, irrespective of the death-induced strategy used (MV-infected or UV-irradiated).

Example 5

Tumor Cells Infected with MV Induce Spontaneous DC Maturation, by Contrast with UV Radiation-Induced Apoptotic M13 Cells The inventors next examined whether cell material derived from MV-infected M13 tumoral cells could efficiently stimulate DC maturation.

DC maturation status was assessed within 24 hours following engulfment of tumoral cells killed either by radiation exposition or virus-mediated cytolytic activity.

Phenotype of viable DCs (gated on basis of TOPRO-3 positive staining exclusion) was investigated by surface expression of Class I and II MHC molecules (FIG. 9) and of maturation markers CD80, CD86, CD83 and CD40 (FIG. 10), completed by cytokines secretion pattern analysis performed on co-culture supernatant (FIG. 11). As controls, DCs were left alone, or matured with a combination of TLR3 ligand and one pro-inflammatory cytokine (polyinosinic: polycytidylic acid/IFNα, as a mimic of viral infection), or directly primed by measles virus contact (MV).

Briefly, immunostaining was performed with a panel of monoclonal antibodies (all purchased from Immunotech, Marseilles, France) specific for HLA-ABC (clone B9.12.1), HLA-DR (clone B8.12.2), CD80 (clone MAB104), CD83 (clone HB15a), CD86 (clone HA5.2B7), and CD40 (clone MAB89). DCs were incubated with each of the above antibodies (1 μg/ml) at 4° C. for 30 min prior to flow cytometry. Cytokines pattern secretion was assayed in supernatants collected 24 hours after engulfment. IL-10, IL-12, IL-6, IL-1β and TNFα concentrations were measured using commercially available Cytometric Beads Array kits (BD Biosciences, Le Pont de Claix, France), according to the manufacturer's protocol. Quantification of IFNα was performed with an ELISA test (Biosource, Camarillo, USA).

A spontaneous maturation program could be observed only for DCs loaded with apobodies derived from mesothelioma cells infected with MV, at a level essentially equivalent to the positive control maturation cocktail used in the experiment (PolyI:C/IFNα). Spontaneous maturation was evidenced by significant up-regulation of co-stimulation molecules expression (for CD80, CD83, CD86, CD40 and HLA-ABC), and production of numerous pro-inflammatory cytokines (for IL-6, IL-1β, TNFα, and IFNα).

However, in line with previous reports, pulsing DCs with UV-irradiated apoptotic tumoral cells, as well as direct infection of DCs by measles virus (MV), did not lead to this effect.

Overall these data strongly support an increased immunogenicity of MV-infected tumoral cells with respect to UV-irradiated tumoral cells.

Example 6

Cross-Priming of MSLN-Specific CD8 T-Cell Response

Finally, the inventors tested whether DCs loaded with apobodies derived from mesothelioma cells infected with MV could stimulate an effector CD8 response specific for an MPM-associated tumor antigen, such as Mesothelin (MSLN).

In order to assess this question, tetramer immunostaining was performed on CD8 T-lymphocytes sensibilized for one-week with autologous DCs loaded with apoptotic material derived from UV- or MV-treated M13 cells. As controls, a similar experiment was conducted with the Jurkat lymphoma T-cell line, chosen on the basis of its susceptibility to MV and its MSLN-negative expression characteristics (FIG. 12). As internal experiment controls, MelanA/Mart-1-specific tetramer staining (MelanA26-35L) was achieved in complement of those specific for the two selected MSLN-derived CTL epitopes. These peptides (MSLN 531-539 and MSLN 541-550) were identified by scanning MSLN amino-acid sequence (GenPept NP 005814) for matches to consensus motifs for HLA-A0201 binding, using two computer algorithms BIMAS and SYFPEITHI (Table 2):

TABLE 2 tetramer characteristics

|  |  |  | HLA-A0201 binding score | |
|---|---|---|---|---|
| Tetramer name | Localisation | Sequence | SYFPEITHI | BIMAS |
| HLA-A2 VLP9 | 531-539 | VLPLTVAEV (SEQ ID NO: 13) | 29/30 | 272/285 |
| HLA-A2 KLL10 | 541-550 | KLLGPHVEGL (SEQ ID NO: 14) | 30/31 | 312/312 |

Briefly, CD8 T lymphocytes were prepared from HLA-A0201 healthy donors PBMCs by positive selection with the MACS column systems using CD8 multisort kit (Miltenyi Biotec, Paris, France). Purified naïve CD8 T cells (>90% purity) were stimulated with autologous DCs loaded with each apoptotic preparation or unloaded DCs as a control. The co-culture was performed in round bottom 96-well plates (BD Falcon), by mixing $2 \cdot 10^4$ mature DCs with $2 \cdot 10^5$ responder T cells (ratio 1:10) in 200 µl of 8% human serum RPMI 1640 medium, supplemented with 10 ng/ml IL-12 for the first 3 days (AbCys SA, Paris, France) and with 10 U/ml IL-2 (Proleukin, Chiron Therapeutics, USA) for the next days. IL-2 was added every three days, allowing regular culture medium renewal. After 7-8 days culture, T cells were harvested and stained with MSLN-specific tetramers as follows.

The selected CD8 epitope peptides (synthesis performed by Eurogentec, Liege, Belgium) were used for monomers production (Recombinant Proteins Production Platform, U601-IFR26, Nantes, France) as previously described (Labarrière et al. (2002) *Int. J. Cancer* 101:280-286). HLA-A2 VLP9 and HLA-A2 KLL10 monomers were oligomerized with PE-labeled streptavidin (BD Biosciences). Staining and washing were performed in 0.1% BSA-PBS. T cells were stained successively with 10 µg/ml of PE-labeled pMHC multimers at 4° C. for 30 min, and with 1 µg/ml diluted PE-Cy5-conjugated anti-CD8 antibodies (clone RPA-T8, BD Biosciences) for additionally 30 min at 4° C. Cells were washed and immediately analysed on a FACSCalibur.

Interestingly, a significant increase of MSLN-specific T-cells percentage among the CD8-positive gated population could be observed for co-cultures with DCs loaded with apoptotic material derived from MV-treated M13 cells with respect to co-cultures with DCs loaded with apoptotic material derived from UV-treated M13 cells.

The invention claimed is:

1. A method for preparing spontaneously mature cancer vaccinal dendritic cells in an individual, comprising the following steps:
   in vitro infection of cancer cells taken from the individual by an attenuated measles strain to yield a cell lysate; and
   contacting dendritic cells with the cell lysate to yield vaccinal dendritic cells which are spontaneously mature,
   wherein said method comprises no step of maturation of said dendritic cells consisting of contacting said dendritic cells with a combination of TLR3 ligand and a pro-inflammatory cytokine.

2. The method according to claim 1, wherein the dendritic cells originate from the individual.

3. The method according to claim 1, wherein the dendritic cells are monocyte-derived dendritic cells.

4. The method according to claim 1, wherein the cancer is malignant mesothelioma.

5. The method according to claim 1, wherein the cancer is malignant pleural mesothelioma.

6. The method according to claim 1, wherein the attenuated measles virus is an Edmonston strain.

7. The method according to claim 1, wherein the attenuated measles virus is selected from the group constituted of a Schwartz strain and a Moraten strain.

8. Vaccinal dendritic cells liable to be obtained by the method according to claim 1.

9. A pharmaceutical composition comprising vaccinal dendritic cells liable to be obtained by the method according to claim 1 as active ingredient, in association with a pharmaceutically acceptable carrier.

10. The method according to claim 1, wherein said spontaneously mature cancer vaccinal dendritic cells significantly over-express CD80, CD83, CD86, CD40 and HLA-ABC and produce IL-6, IL-1β, TNFα and IFNα.

11. The method according to claim 1, wherein the cancer is peritoneal mesothelioma.

* * * * *

SEQUENCE LISTING

```
<160> NUMBER OF SEQ ID NOS: 14

<210> SEQ ID NO 1
<211> LENGTH: 18967
<212> TYPE: DNA
<213> ORGANISM: Artificial sequence
<220> FEATURE:
<223> OTHER INFORMATION: Plasmid pTM-MVSchw

<400> SEQUENCE: 1
gcggccgcta atacgactca ctatagggcc aactttgttt ggtctgatga gtccgtgagg      60
acgaaacccg gagtcccggg tcaccaaaca aagttgggta aggatagttc aatcaatgat     120
catcttctag tgcacttagg attcaagatc ctattatcag ggacaagagc aggattaggg     180
atatccgaga tggccacact tttaaggagc ttagcattgt tcaaaagaaa caaggacaaa     240
ccacccatta catcaggatc cggtggagcc atcaggagaa tcaaacacat tattatagta     300
ccaatccctg gagattcctc aattaccact cgatccagac ttctggaccg gttggtgagg     360
ttaattggaa acccggatgt gagcgggccc aaactaacag gggcactaat aggtatatta     420
tccttatttg tggagtctcc aggtcaattg attcagagga tcaccgatga ccctgacgtt     480
agcataaggc tgttagaggt tgtccagagt gaccagtcac aatctggcct taccttcgca     540
tcaagaggta ccaacatgga ggatgaggcg gaccaatact tttcacatga tgatccaatt     600
agtagtgatc aatccaggtt cggatggttc gggaacaagg aaatctcaga tattgaagtg     660
caagaccctg agggattcaa catgattctg ggtaccatcc tagcccaaat ttgggtcttg     720
ctcgcaaagg cggttacggc cccagacacg gcagctgatt cggagctaag aaggtggata     780
aagtacaccc aacaaagaag ggtagttggt gaatttagat tggagagaaa atggttggat     840
```

```
gtggtgagga acaggattgc cgaggacctc tccttacgcc gattcatggt cgctctaatc    900
ctggatatca agagaacacc cggaaacaaa cccaggattg ctgaaatgat atgtgacatt    960
gatacatata tcgtagaggc aggattagcc agttttatcc tgactattaa gtttgggata   1020
gaaactatgt atcctgctct tggactgcat gaatttgctg gtgagttatc cacacttgag   1080
tccttgatga accttttacca gcaaatgggg gaaactgcac cctacatggt aatcctggag   1140
aactcaattc agaacaagtt cagtgcagga tcatacccctc tgctctggag ctatgccatg   1200
ggagtaggag tggaacttga aaactccatg ggaggtttga actttggccg atcttacttt   1260
gatccagcat attttagatt agggcaagag atggtaagga ggtcagctgg aaaggtcagt   1320
tccacattgg catctgaact cggtatcact gccgaggatg caaggcttgt ttcagagatt   1380
gcaatgcata ctactgagga caagatcagt agagcggttg acccagaca agcccaagta   1440
tcatttctac acggtgatca aagtgagaat gagctaccga gattgggggg caaggaagat   1500
aggagggtca aacagagtcg aggagaagcc agggagagct acagagaaac cgggcccagc   1560
agagcaagtg atgcgagagc tgcccatctt ccaaccggca caccctaga cattgacact   1620
gcaacggagt ccagccaaga tccgcaggac agtcgaaggt cagctgacgc cctgcttagg   1680
ctgcaagcca tggcaggaat ctcggaagaa caaggctcag acacgacac ccctatagtg   1740
tacaatgaca gaaatcttct agactaggtg cgagaggccg agggccagaa caacatccgc   1800
ctaccatcca tcattgttat aaaaaactta ggaaccaggt ccacacagcc gccagcccat   1860
caaccatcca ctcccacgat tggagccaat ggcagaagag caggcacgcc atgtcaaaaa   1920
cggactggaa tgcatcccggg ctctcaaggc cgagcccatc ggctcactgg ccatcgagga   1980
agctatggca gcatggtcag aaatatcaga caacccagga caggagcgag ccacctgcag   2040
ggaagagaag gcaggcagtt cgggtctcag caaaccatgc ctctcagcaa ttggatcaac   2100
tgaaggcggt gcacctcgca tccgcggtca gggacctgga gagagcgatg acgacgctga   2160
aactttggga atcccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga acaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaagggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg ggaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
```

```
gtttgttcct gacaccggcc ctgcatcacg cagtgtaatc cgctccatta taaaatccag    3300
ccggctagag gaggatcgga agcgttacct gatgactctc cttgatgata tcaaaggagc    3360
caatgatctt gccaagttcc accagatgct gatgaagata taatgaagt agctacagct     3420 caacttacct gccaacccca tgccagtcga cccaactagt acaacctaaa tccattataa    3480
aaaacttagg agcaaagtga ttgcctccca aggtccacaa tgacagagac ctacgacttc    3540
gacaagtcgg catgggacat caaagggtcg atcgctccga tacaacccac cacctacagt    3600
gatggcaggc tggtgcccca ggtcagagtc atagatcctg gtctaggcga caggaaggat    3660
gaatgcttta tgtacatgtt tctgctgggg gttgttgagg acagcgattc cctagggcct    3720
ccaatcgggc gagcatttgg gttcctgccc ttaggtgttg gcagatccac agcaaagccc    3780
gaaaaactcc tcaaagaggc cactgagctt gacatagttg ttagacgtac agcagggctc    3840
aatgaaaaac tggtgttcta acaacacacc ccactaactc tcctcacacc ttggagaaag    3900
gtcctaacaa cagggagtgt cttcaacgca aaccaagtgt gcaatgcggt taatctgata    3960
ccgctcgata ccccgcagag gttccgtgtt gtttatatga gcatcacccg tctttcggat    4020
aacgggtatt acaccgttcc tagaagaatg ctggaattca gatcggtcaa tgcagtggcc    4080
ttcaacctgc tggtgaccct taggattgac aaggcgatag gccctgggaa gatcatcgac    4140
aatacagagc aacttcctga ggcaacattt atggtccaca tcgggaactt caggagaaag    4200
aagagtgaag tctactctgc cgattattgc aaaatgaaaa tcgaaaagat gggcctggtt    4260
tttgcacttg gtgggatagg gggcaccagt cttcacatta gaagcacagg caaaatgagc    4320
aagactctcc atgcacaact cgggttcaag aagaccttat gttacccgct gatggatatc    4380
aatgaagacc ttaatcgatt actctggagg agcagatgca agatagtaag aatccaggca    4440
gttttgcagc catcagttcc tcaagaattc cgcatttacg acgacgtgat cataaatgat    4500
gaccaaggac tattcaaagt tctgtagacc gtagtgccca gcaatgcccg aaaacgaccc    4560
ccctcacaat gacagccaga aggcccggac aaaaaagccc cctccgaaag actccacgga    4620
ccaagcgaga ggccagccag cagccgacgg caagcgcgaa caccaggcgg ccccagcaca    4680
gaacagccct gacacaaggc caccaccagc cacccccaatc tgcatcctcc tcgtgggacc    4740
cccgaggacc aaccccccaag gctgcccccg atccaaacca ccaaccgcat ccccaccacc    4800
cccgggaaag aaacccccag caattggaag gcccctcccc ctcttcctca acacaagaac    4860
tccacaaccg aaccgcacaa gcgaccgagg tgacccaacc gcaggcatcc gactccctag    4920
acagatcctc tctccccggc aaactaaaca aaacttaggg ccaaggaaca tacacaccca    4980
acagaaccca gaccccggcc cacggcgccg cgccccccaac cccgacaac cagagggagc     5040 ccccaaccaa tccgccggc tcccccggtg cccacaggca gggacaccaa ccccgaaca      5100 gacccagcac ccaaccatcg acaatccaag acgggggggc cccccaaaa aaggccccc      5160 aggggccgac agccagcacc gcgaggaagc ccacccaccc cacacacgac cacggcaacc    5220
aaaccagaac ccagaccacc ctgggccacc agctcccaga ctcggccatc accccgcaga    5280
aaggaaaggc cacaacccgc gcaccccagc cccgatccgg cggggagcca cccaacccga    5340
accagcaccc aagagcgatc cccgaaggac ccccgaaccg caaaggacat cagtatccca    5400
cagcctctcc aagtcccccg gtctcctcct cttctcgaag ggaccaaaag atcaatccac    5460
cacacccgac gacactcaac tccccacccc taaaggagac accgggaatc ccagaatcaa    5520
gactcatcca atgtccatca tgggtctcaa ggtgaacgtc tctgccatat tcatggcagt    5580
```

```
actgttaact ctccaaacac ccaccggtca aatccattgg ggcaatctct ctaagatagg    5640
ggtggtagga ataggaagtg caagctacaa agttatgact cgttccagcc atcaatcatt    5700
agtcataaaa ttaatgccca atataactct cctcaataac tgcacgaggg tagagattgc    5760
agaatacagg agactactga gaacagtttt ggaaccaatt agagatgcac ttaatgcaat    5820
gacccagaat ataagaccgg ttcagagtgt agcttcaagt aggagacaca agagatttgc    5880
gggagtagtc ctggcaggtg cggccctagg cgttgccaca gctgctcaga taacagccgg    5940
cattgcactt caccagtcca tgctgaactc tcaagccatc gacaatctga gagcgagcct    6000
ggaaactact aatcaggcaa ttgagacaat cagacaagca gggcaggaga tgatattggc    6060
tgttcagggt gtccaagact acatcaataa tgagctgata ccgtctatga accaactatc    6120
ttgtgattta atcggccaga agctcgggct caaattgctc agatactata cagaaatcct    6180
gtcattattt ggccccagtt tacgggaccc catatctgcg gagatatcta tccaggcttt    6240
gagctatgcg cttggaggag acatcaataa ggtgttagaa aagctcggat acagtggagg    6300
tgatttactg ggcatcttag agagcggagg aataaaggcc cggataactc acgtcgacac    6360
agagtcctac ttcattgtcc tcagtatagc ctatccgacg ctgtccgaga ttaagggggt    6420
gattgtccac cggctagagg gggtctcgta caacataggc tctcaagagt ggtataccac    6480
tgtgcccaag tatgttgcaa cccaagggta ccttatctcg aattttgatg agtcatcgtg    6540
tactttcatg ccagagggga ctgtgtgcag ccaaaatgcc ttgtacccga tgagtcctct    6600
gctccaagaa tgcctccggg ggtacaccaa gtcctgtgct cgtacactcg tatccgggtc    6660
ttttgggaac cggttcattt tatcacaagg gaacctaata gccaattgtg catcaatcct    6720
ttgcaagtgt tacacaacag gaacgatcat taatcaagac cctgacaaga tcctaacata    6780
cattgctgcc gatcactgcc cggtagtcga ggtgaacggc gtgaccatcc aagtcgggag    6840
caggaggtat ccagacgctg tgtacttgca cagaattgac ctcggtcctc ccatatcatt    6900
ggagaggttg gacgtaggga caaatctggg gaatgcaatt gctaagttgg aggatgccaa    6960
ggaattgttg gagtcatcgg accagatatt gaggagtatg aaaggtttat cgagcactag    7020
catagtctac atcctgattg cagtgtgtct tggagggttg atagggatcc ccgctttaat    7080
atgttgctgc aggggggcgtt gtaacaaaaa gggagaacaa gttggtatgt caagaccagg    7140
cctaaagcct gatcttacgg gaacatcaaa atcctatgta aggtcgctct gatcctctac    7200
aactcttgaa acacaaatgt cccacaagtc tcctcttcgt catcaagcaa ccaccgcacc    7260
cagcatcaag cccaccctgaa attatctccg gcttccctct ggccgaacaa tatcggtagt    7320
taatcaaaac ttagggtgca agatcatcca caatgtcacc acaacgagac cggataaatg    7380
ccttctacaa agataacccc catcccaagg gaagtaggat agtcattaac agagaacatc    7440
ttatgattga tagaccttat gttttgctgg ctgttctgtt tgtcatgttt ctgagcttga    7500
tcgggttgct agccattgca ggcattagac ttcatcgggc agccatctac accgcagaga    7560
tccataaaag cctcagcacc aatctagatg taactaactc aatcgagcat caggtcaagg    7620
acgtgctgac accactcttc aaaatcatcg gtgatgaagt gggcctgagg acacctcaga    7680
gattcactga cctagtgaaa ttaatctctg acaagattaa attccttaat ccggataggg    7740
agtacgactt cagagatctc acttggtgta tcaacccgcc agagagaatc aaattggatt    7800
atgatcaata ctgtgcagat gtggctgctg aagagctcat gaatgcattg gtgaactcaa    7860
ctctactgga gaccagaaca accaatcagt tcctagctgt ctcaaaggga aactgctcag    7920
ggcccactac aatcagaggt caattctcaa acatgtcgct gtccctgtta gacttgtatt    7980
```

```
taggtcgagg ttacaatgtg tcatctatag tcactatgac atcccaggga atgtatgggg    8040
gaacttacct agtggaaaag cctaatctga gcagcaaaag gtcagagttg tcacaactga    8100
gcatgtaccg agtgtttgaa gtaggtgtta tcagaaatcc gggtttgggg gctccggtgt    8160
tccatatgac aaactatctt gagcaaccag tcagtaatga tctcagcaac tgtatggtgg    8220
ctttggggga gctcaaactc gcagcccttt gtcacgggga agattctatc acaattccct    8280
atcagggatc agggaaaggt gtcagcttcc agctcgtcaa gctaggtgtc tggaaatccc    8340
caaccgacat gcaatcctgg gtccccttat caacggatga tccagtgata gacaggcttt    8400
acctctcatc tcacagaggt gttatcgctg acaatcaagc aaaatgggct gtcccgacaa    8460
cacgaacaga tgacaagttg cgaatggaga catgcttcca acaggcgtgt aagggtaaaa    8520
tccaagcact ctgcgagaat cccgagtggg caccattgaa ggataacagg attccttcat    8580
acggggtctt gtctgttgat ctgagtctga cagttgagct taaaatcaaa attgcttcgg    8640
gattcgggcc attgatcaca cacggttcag ggatggacct atacaaatcc aaccacaaca    8700
atgtgtattg gctgactatc ccgccaatga agaacctagc cttaggtgta atcaacacat    8760
tggagtggat accgagattc aaggttagtc cctacctctt cactgtccca attaaggaag    8820
caggcgaaga ctgccatgcc ccaacatacc tacctgcgga ggtggatggt gatgtcaaac    8880
tcagttccaa tctggtgatt ctacctggtc aagatctcca atatgttttg gcaacctacg    8940
atacttccag ggttgaacat gctgtggttt attacgttta cagcccaagc cgctcatttt    9000
cttactttta tccttttagg ttgcctataa agggggtccc catcgaatta caagtggaat    9060
gcttcacatg ggaccaaaaa ctctggtgcc gtcacttctg tgtgcttgcg gactcagaat    9120
ctggtggaca tatcactcac tctgggatgg tgggcatggg agtcagctgc acagtcaccc    9180
gggaagatgg aaccaatcgc agatagggct gctagtgaac caatcacatg atgtcaccca    9240
gacatcaggc ataccactag tgtgaaaata gacatcagaa ttaagaaaaa cgtagggtcc    9300
aagtggttcc ccgttatgga ctcgctatct gtcaaccaga tcttatacccc tgaagttcac    9360 ctagatagcc cgatagttac caataagata gtagccatcc tggagtatgc tcgagtccct    9420
cacgcttaca gcctggagga ccctacactg tgtcagaaca tcaagcaccg cctaaaaaac    9480
ggattttcca accaaatgat tataaacaat gtggaagttg ggaatgtcat caagtccaag    9540
cttaggagtt atccggccca ctctcatatt ccatatccaa attgtaatca ggatttattt    9600
aacatagaag acaaagagtc aacgaggaag atccgtgaac tcctcaaaaa ggggaattcg    9660
ctgtactcca aagtcagtga taaggttttc caatgcttaa gggacactaa ctcacggctt    9720
ggcctaggct ccgaattgag ggaggacatc aaggagaaag ttattaactt gggagtttac    9780
atgcacagct cccagtggtt tgagcccttt ctgttttggt ttcagtcaa gactgagatg    9840 aggtcagtga ttaaatcaca aacccatact tgccatagga ggagacacac acctgtattc    9900
ttcactggta gttcagttga gttgctaatc tctcgtgacc ttgttgctat aatcagtaaa    9960
gagtctcaac atgtatatta cctgacattt gaactggttt tgatgtattg tgatgtcata   10020
gaggggaggt taatgacaga gaccgctatg actattgatg ctaggtatac agagcttcta   10080
ggaagagtca gatacatgtg gaaactgata gatggtttct tccctgcact cgggaatcca   10140
acttatcaaa ttgtagccat gctggagcct ctttcacttg cttacctgca gctgagggat   10200
ataacagtag aactcagagg tgctttcctt aaccactgct ttactgaaat acatgatgtt   10260
cttgaccaaa acgggttttc tgatgaaggt acttatcatg agttaactga agctctagat   10320
```

```
tacattttca taactgatga catacatctg acaggggaga ttttctcatt tttcagaagt    10380
ttcggccacc ccagacttga agcagtaacg gctgctgaaa atgttaggaa atacatgaat    10440
cagcctaaag tcattgtgta tgagactctg atgaaaggtc atgccatatt tgtggaatc    10500
ataatcaacg gctatcgtga caggcacgga ggcagttggc caccgctgac cctcccctg    10560
catgctgcag acacaatccg gaatgctcaa gcttcaggtg aagggttaac acatgagcag    10620
tgcgttgata actggaaatc ttttgctgga gtgaaatttg gctgctttat gcctcttagc    10680
ctggatagtg atctgacaat gtacctaaag gacaaggcac ttgctgctct ccaaagggaa    10740
tgggattcag tttacccgaa agagttcctg cgttacgacc ctcccaaggg aaccgggtca    10800
cggaggcttg tagatgtttt ccttaatgat tcgagctttg acccatatga tgtgataatg    10860
tatgttgtaa gtggagctta cctccatgac cctgagttca acctgtctta cagcctgaaa    10920
gaaaaggaga tcaaggaaac aggtagactt tttgctaaaa tgacttacaa aatgagggca    10980
tgccaagtga ttgctgaaaa tctaatctca aacgggattg gcaaatattt taaggacaat    11040
gggatggcca aggatgagca cgatttgact aaggcactcc acactctagc tgtctcagga    11100
gtccccaaag atctcaaaga aagtcacagg gggggccag tcttaaaaac ctactcccga    11160
agcccagtcc acacaagtac caggaacgtg agagcagcaa aagggtttat agggttccct    11220
caagtaattc ggcaggacca agacactgat catccggaga atatggaagc ttacgagaca    11280
gtcagtgcat ttatcacgac tgatctcaag aagtactgcc ttaattggag atatgagacc    11340
atcagcttgt ttgcacagag gctaaatgag atttacggat tgccctcatt tttccagtgg    11400
ctgcataaga ggcttgagac ctctgtcctg tatgtaagtg accctcattg ccccccccgac    11460
cttgacgccc atatcccgtt atataaagtc cccaatgatc aaatcttcat taagtaccct    11520
atgggaggta tagaagggta ttgtcagaag ctgtggacca tcagcaccat tccctatcta    11580
tacctggctg cttatgagag cggagtaagg attgcttcgt tagtgcaagg ggacaatcag    11640
accatagccg taacaaaaag ggtacccagc acatggccct acaaccttaa gaaacgggaa    11700
gctgctagag taactagaga ttactttgta attcttaggc aaaggctaca tgatattggc    11760
catcacctca aggcaaatga gacaattgtt tcatcacatt ttttttgtcta ttcaaaagga    11820
atatattatg atgggctact tgtgtcccaa tcactcaaga gcatcgcaag atgtgtattc    11880
tggtcagaga ctatagttga tgaaacaagg gcagcatgca gtaatattgc tacaacaatg    11940
gctaaaagca tcgagagagg ttatgaccgt taccttgcat attccctgaa cgtcctaaaa    12000
gtgatacagc aaattctgat ctctcttggc ttcacaatca attcaaccat gacccgggat    12060
gtagtcatac ccctcctcac aaacaacgac ctcttaataa ggatggcact gttgcccgct    12120
cctattgggg ggatgaatta tctgaatatg agcaggctgt tgtcagaaa catcggtgat    12180
ccagtaacat catcaattgc tgatctcaag agaatgatte tcgcctcact aatgcctgaa    12240
gagaccctcc atcaagtaat gacacaacaa ccgggggact cttcattcct agactgggct    12300
agcgacccctt actcagcaaa tcttgtatgt gtccagagca tcactagact cctcaagaac    12360
ataactgcaa ggtttgtcct gatccatagt ccaaacccaa tgttaaaagg attattccat    12420
gatgacagta agaagagga cgagggactg gcggcattcc tcatggacag gcatattata    12480
gtacctaggg cagctcatga aatcctggat catagtgtca caggggcaag agagtctatt    12540
gcaggcatgc tggatacccac aaaaggcttg attcgagcca gcatgaggaa gggggggtta    12600
acctctcgag tgataaccag attgtccaat tatgactatg aacaattcag agcagggatg    12660
gtgctattga caggaagaaa gagaaatgtc ctcattgaca aagagtcatg ttcagtgcag    12720
```

```
ctggcgagag ctctaagaag ccatatgtgg gcgaggctag ctcgaggacg gcctatttac   12780
ggccttgagg tccctgatgt actagaatct atgcgaggcc accttattcg gcgtcatgag   12840
acatgtgtca tctgcgagtg tggatcagtc aactacggat ggttttttgt cccctcgggt   12900
tgccaactgg atgatattga caaggaaaca tcatccttga gagtcccata tattggttct   12960
accactgatg agagaacaga catgaagctt gccttcgtaa gagccccaag tcgatccttg   13020
cgatctgctg ttagaatagc aacagtgtac tcatgggctt acggtgatga tgatagctct   13080
tggaacgaag cctggttgtt ggctaggcaa agggccaatg tgagcctgga ggagctaagg   13140
gtgatcactc ccatctcaac ttcgactaat ttagcgcata ggttgaggga tcgtagcact   13200
caagtgaaat actcaggtac atcccttgtc cgagtggcga ggtataccac aatctccaac   13260
gacaatctct catttgtcat atcagataag aaggttgata ctaactttat ataccaacaa   13320
ggaatgcttc tagggttggg tgttttagaa acattgtttc gactcgagaa agataccgga   13380
tcatctaaca cggtattaca tcttcacgtc gaaacagatt gttgcgtgat cccgatgata   13440
gatcatccca ggatacccag ctcccgcaag ctagagctga gggcagagct atgtaccaac   13500
ccattgatat atgataatgc acctttaatt gacagagatg caacaaggct atacacccag   13560
agccatagga ggcaccttgt ggaatttgtt acatggtcca cccccaact atatcacatt   13620 ttagctaagt ccacagcact atctatgatt gacctggtaa caaaatttga gaaggaccat   13680
atgaatgaaa tttcagctct catagggat gacgatatca atagtttcat aactgagttt   13740
ctgctcatag agccaagatt attcactatc tacttgggcc agtgtgcggc catcaattgg   13800
gcatttgatg tacattatca tagaccatca gggaaatatc agatgggtga gctgttgtca   13860
tcgttccttt ctagaatgag caaaggagtg tttaaggtgc ttgtcaatgc tctaagccac   13920
ccaaagatct acaagaaatt ctggcattgt ggtattatag agcctatcca tggtccttca   13980
cttgatgctc aaaacttgca cacaactgtg tgcaacatgg tttacacatg ctatatgacc   14040
tacctcgacc tgttgttgaa tgaagagtta aagagttca catttctctt gtgtgaaagc   14100
gacgaggatg tagtaccgga cagattcgac aacatccagg caaaacactt atgtgttctg   14160
gcagatttgt actgtcaacc agggacctgc ccaccaattc gaggtctaag accggtagag   14220
aaatgtgcag ttctaaccga ccatatcaag gcagaggcta tgttatctcc agcaggatct   14280
tcgtggaaca taaatccaat tattgtagac cattactcat gctctctgac ttatctccgg   14340
cgaggatcga tcaaacagat aagattgaga gttgatccag gattcatttt cgacgccctc   14400
gctgaggtaa atgtcagtca gccaaagatc ggcagcaaca acatctcaaa tatgagcatc   14460
aaggctttca gaccccccaca cgatgatgtt gcaaaattgc tcaaagatat caacacaagc   14520
aagcacaatc ttcccatttc aggggcaat ctcgccaatt atgaaatcca tgctttccgc   14580
agaatcgggt tgaactcatc tgcttgctac aaagctgttg agatatcaac attaattagg   14640
agatgccttg agccagggga ggacggcttg ttcttgggtg agggatcggg ttctatgttg   14700
atcacttata aagagatact taaactaaac aagtgcttct ataatagtgg ggtttccgcc   14760
aattctagat ctggtcaaag ggaattagca ccctatccct ccgaagttgg ccttgtcgaa   14820
cacagaatgg gagtaggtaa tattgtcaaa gtgctcttta cgggaggcc cgaagtcacg   14880 tgggtaggca gtgtagattg cttcaatttc atagttagta atatccctac ctctagtgtg   14940
gggtttatcc attcagatat agagaccttg cctgacaaag atactataga gaagctagag   15000
gaattggcag ccatcttatc gatggctctg ctcctgggca aaataggatc aatactggtg   15060
```

```
attaagctta tgcctttcag cggggatttt gttcagggat ttataagtta tgtagggtct   15120
cattatagag aagtgaacct tgtataccct agatacagca acttcatctc tactgaatct   15180
tatttggtta tgacagatct caaggctaac cggctaatga atcctgaaaa gattaagcag   15240
cagataattg aatcatctgt gaggacttca cctggactta taggtcacat cctatccatt   15300
aagcaactaa gctgcataca agcaattgtg ggagacgcag ttagtagagg tgatatcaat   15360
cctactctga aaaacttac acctatagag caggtgctga tcaattgcgg gttggcaatt    15420
aacggaccta agctgtgcaa agaattgatc caccatgatg ttgcctcagg gcaagatgga   15480
ttgcttaatt ctatactcat cctctacagg gagttggcaa gattcaaaga caaccaaaga   15540
agtcaacaag ggatgttcca cgcttacccc gtattggtaa gtagcaggca acgagaactt   15600
atatctagga tcacccgcaa attctggggg cacattcttc tttactccgg gaacaaaaag   15660
ttgataaata agtttatcca gaatctcaag tccggctatc tgatactaga cttacaccag   15720
aatatcttcg ttaagaatct atccaagtca gagaaacaga ttattatgac gggggggtttg   15780
aaacgtgagt gggttttaa ggtaacagtc aaggagacca agaatggta taagttagtc     15840
ggatacagtg ccctgattaa ggactaattg gttgaactcc ggaaccctaa tcctgcccta   15900
ggtggttagg cattatttgc aatatattaa agaaaacttt gaaaatacga gtttctatt    15960
cccagctttg tctggtggcc ggcatggtcc cagcctcctc gctggcgccg gctgggcaac   16020
attccgaggg gaccgtcccc tcggtaatgg cgaatgggac gcggccgatc cggctgctaa   16080
caaagcccga aggaagctg agttggctgc tgccaccgct gagcaataac tagcataacc    16140
ccttggggcc tctaaacggg tcttgagggg ttttttgctg aaaggaggaa ctatatccgg   16200
atgcggccgc gggccctatg gtacccagct tttgttccct ttagtgaggg ttaattccga   16260
gcttggcgta atcatggtca tagctgtttc ctgtgtgaaa ttgttatccg ctcacaattc   16320
cacacaacat aggagccgga agcataaagt gtaaagcctg gggtgcctaa tgagtgaggt   16380
aactcacatt aattgcgttg cgctcactgc ccgctttcca gtcgggaaac ctgtcgtgcc   16440
agctgcatta atgaatcggc caacgcgcgg ggagaggcgg tttgcgtatt gggcgctctt   16500
ccgcttcctc gctcactgac tcgctgcgct cggtcgttcg ctgcggcga gcggtatcag    16560
ctcactcaaa ggcggtaata cggttatcca cagaatcagg ggataacgca ggaaagaaca   16620
tgtgagcaaa aggccagcaa aaggccagga accgtaaaaa ggccgcgttg ctggcgtttt   16680
tccataggct cggcccccct gacgagcatc acaaaaatcg acgctcaagt cagaggtggc   16740
gaaacccgac aggactataa agataccagg cgttcccccc tggaagctcc ctcgtgcgct   16800
ctcctgttcc gaccctgccg cttaccggat acctgtccgc ctttctccct cgggaagcg    16860
tggcgctttc tcaatgctca cgctgtaggt atctcagttc ggtgtaggtc gttcgctcca   16920
agctgggctg tgtgcacgaa ccccccgttc agcccgaccg ctgcgcctta ccggtaact    16980
atcgtcttga gtccaacccg gtaagacacg acttatcgcc actggcagca gccactggta   17040
acaggattag cagagcgagg tatgtaggcg gtgctacaga gttcttgaag tggtggccta   17100
actacggcta cactagaagg acagtatttg gtatctgcgc tctgctgaag ccagttacct   17160
tcggaaaaag agttggtagc tcttgatccg gcaaacaaac caccgctggt agcggtggtt   17220
ttttgtttg caagcagcag attacgcgca gaaaaaaagg atctcaagaa gatcctttga    17280
tcttttctac ggggtctgac gctcagtgga acgaaaactc acgttaaggg attttggtca   17340
tgagattatc aaaaaggatc ttcacctaga tccttttaaa ttaaaaatga agttttaaat   17400
caatctaaag tatatatgag taaacttggt ctgacagtta ccaatgctta atcagtgagg   17460
```

-continued

```
cacctatctc agcgatctgt ctatttcgtt catccatagt tgcctgactg cccgtcgtgt    17520
agataactac gatacgggag ggcttaccat ctggccccag tgctgcaatg ataccgcgag    17580
acccacgctc accggctcca gatttatcag caataaacca gccagccgga agggccgagc    17640
gcagaagtgg tcctgcaact ttatccgcct ccatccagtc tattaattgt tgccgggaag    17700
ctagagtaag tagttcgcca gttaatagtt tgcgcaacgt tgttgccatt gctacaggca    17760
tcgtggtgtc acgctcgtcg tttggtatgg cttcattcag ctccggttcc caacgatcaa    17820
ggcgagttac atgatccccc atgttgtgaa aaaagcggt tagctccttc ggtcctccga    17880
tcgttgtcag aagtaagttg gccgcagtgt tatcactcat gcttatggca gcactgcata    17940
attctcttac tgtcatgcca tccgtaagat gcttttctgt gactggtgag tactcaacca    18000
agtcattctg agaatagtgt atgcggcgac cgagttgctc ttgcccggcg tcaatacggg    18060
ataataccgc gccacatagc agaactttaa aagtgctcat cattggaaaa cgttcttcgg    18120
ggcgaaaact ctcaaggatc ttaccgctgt tgagatccag ttcgatgtaa cccactcgtg    18180
cacccaactg atcttcagca tcttttactt tcaccagcgt ttctgggtga gcaaaaacag    18240
gaaggcaaaa tgccgcaaaa aagggaataa gggcgacacg gaaatgttga atactcatac    18300
tcttcctttt tcaatattat tgaagcattt atcagggtta ttgtctcatg agcggataca    18360
tatttgaatg tatttagaaa aataaacaaa taggggttcc gcgcacattt ccccgaaaag    18420
tgccacctga aattgtaaac gttaatattt tgttaaaatt cgcgttaaat ttttgttaaa    18480
tcagctcatt ttttaaccaa taggccgaaa tcggcaaaat cccttataaa tcaaaagaat    18540
agaccgagat agggttgagt gttgttccag tttggaacaa gagtccacta ttaaagaacg    18600
tggactccaa cgtcaaaggg cgaaaaaccg tctatcaggg cgatggccca ctacgtgaac    18660
catcacccta atcaagtttt tggggtcga ggtgccgtaa agcactaaat cggaaccta    18720 aagggagccc ccgatttaga gcttgacggg gaaagccggc gaacgtggcg agaaggaag    18780 ggaagaaagc gaaaggagcg ggcgctaggg cgctggcaag tgtagcggtc acgctgcgcg    18840
taaccaccac acccgccgcg cttaatgcgc cgctacaggg cgcgtcccat tcgccattca    18900
ggctgcgcaa ctgttgggaa gggcgatcgg tgcgggcctc ttcgctatta cgccagccac    18960
cgcggtg                                                              18967
```

<210> SEQ ID NO 2
<211> LENGTH: 12082
<212> TYPE: DNA
<213> ORGANISM: Artificial sequence
<220> FEATURE:
<223> OTHER INFORMATION: Plasmid pEMC-LSchw

<400> SEQUENCE: 2

```
aagcttttgc gatcaataaa tggatcacaa ccagtatctc ttaacgatgt tcttcgcaga      60
tgatgattca ttttttaagt atttggctag tcaagatgat gaatcttcat tatctgatat     120
attgcaaatc actcaatatc tagactttct gttattatta ttgatccaat caaaaaataa     180
attagaagcc gtgggtcatt gttatgaatc tctttcagag gaatacagac aattgacaaa     240
attcacagac tttcaagatt ttaaaaaact gtttaacaag gtccctattg ttacagatgg     300
aagggtcaaa cttaataaag gatatttgtt cgactttgtg attagtttga tgcgattcaa     360
aaaagaatcc tctctagcta ccaccgcaat agatcctgtt agatacatag atcctcgtcg     420
caatatcgca ttttctaacg tgatggatat attaaagtcg aataaagtga acaataatta     480
```

```
attctttatt gtcatcatga acggcggaca tattcagttg ataatcggcc ccatgttttc      540
aggtaaaagt acagaattaa ttagacgagt tagacgttat caaatagctc aatataaatg      600
cgtgactata aaatattcta acgataatag atacggaacg ggactatgga cgcatgataa      660
gaataatttt gaagcattgg aagcaactaa actatgtgat gtcttggaat caattacaga      720
tttctccgtg ataggtatcg atgaaggaca gttctttcca gacattgttg aattgatctc      780
gatcccgcga aattaatacg actcactata gggagaccac aacggtttcc ctctagcggg      840
atcaattccg cccctctccc tccccccccc ctaacgttac tggccgaagc cgcttggaat      900
aaggccggtg tgcgtttgtc tatatgttat tttccaccat attgccgtct tttggcaatg      960
tgagggcccg gaaacctggc cctgtcttct tgacgagcat tcctaggggt ctttcccctc     1020
tcgccaaagg aatgcaaggt ctgttgaatg tcgtgaagga agcagttcct ctggaagctt     1080
cttgaagaca acaacgtct gtagcgaccc tttgcaggca gcggaacccc ccacctggcg     1140
acaggtgcct ctgcggccaa aagccacgtg tataagatac acctgcaaag gcggcacaac     1200
cccagtgcca cgttgtgagt tggatagttg tggaaagagt caaatggctc tcctcaagcg     1260
tattcaacaa ggggctgaag gatgcccaga aggtacccca ttgtatggga tctgatctgg     1320
ggcctcggtg cacatgcttt acatgtgttt agtcgaggtt aaaaaacgtc taggccccc      1380 gaaccacggg gacgtggttt tcctttgaaa aacacgataa taccatggac tcgctatctg     1440
tcaaccagat cttatacct gaagttcacc tagatagccc gatagttacc aataagatag     1500
tagccatcct ggagtatgct cgagtccctc acgcttacag cctggaggac cctacactgt     1560
gtcagaacat caagcaccgc ctaaaaaacg gattttccaa ccaaatgatt ataaacaatg     1620
tggaagttgg gaatgtcatc aagtccaagc ttaggagtta tccggcccac tctcatattc     1680
catatccaaa ttgtaatcag gatttattta acatagaaga caaagagtca acgaggaaga     1740
tccgtgaact cctcaaaaag gggaattcgc tgtactccaa agtcagtgat aaggttttcc     1800
aatgcttaag ggacactaac tcacggcttg gcctaggctc cgaattgagg gaggacatca     1860
aggagaaagt tattaacttg ggagtttaca tgcacagctc ccagtggttt gagccctttc     1920
tgttttggtt tacagtcaag actgagatga ggtcagtgat taaatcacaa acccatactt     1980
gccataggag gagacacaca cctgtattct tcactggtag ttcagttgag ttgctaatct     2040
ctcgtgacct tgttgctata atcagtaaag agtctcaaca tgtatattac ctgacatttg     2100
aactggtttt gatgtattgt gatgtcatag agggaggtt aatgacagag accgctatga     2160
ctattgatgc taggtataca gagcttctag gaagagtcag atacatgtgg aaactgatag     2220
atggtttctt ccctgcactc gggaatccaa cttatcaaat tgtagccatg ctggagcctc     2280
tttcacttgc ttacctgcag ctgagggata aacagtaga actcagaggt gctttcctta     2340
accactgctt tactgaaata catgatgttc ttgaccaaaa cgggttttct gatgaaggta     2400
cttatcatga gttaactgaa gctctagatt acattttcat aactgatgac atacatctga     2460
caggggagat tttctcattt ttcagaagtt tcggccaccc cagacttgaa gcagtaacgg     2520
ctgctgaaaa tgttaggaaa tacatgaatc agcctaaagt cattgtgtat gagactctga     2580
tgaaaggtca tgccatattt tgtggaatca taatcaacgg ctatcgtgac aggcacggag     2640
gcagttggcc accgctgacc ctccccctgc atgctgcaga cacaatccgg aatgctcaag     2700
cttcaggtga agggtaaca catgagcagt gcgttgataa ctggaaatct tttgctggag     2760
tgaaatttgg ctgctttatg cctcttagcc tggatagtga tctgacaatg tacctaaagg     2820
acaaggcact tgctgctctc caaagggaat gggattcagt ttacccgaaa gagttcctgc     2880
```

```
gttacgaccc tcccaaggga accgggtcac ggaggcttgt agatgttttc cttaatgatt    2940
cgagctttga cccatatgat gtgataatgt atgttgtaag tggagcttac ctccatgacc    3000
ctgagttcaa cctgtcttac agcctgaaag aaaaggagat caaggaaaca ggtagacttt    3060
ttgctaaaat gacttacaaa atgagggcat gccaagtgat tgctgaaaat ctaatctcaa    3120
acgggattgg caaatatttt aaggacaatg ggatggccaa ggatgagcac gatttgacta    3180
aggcactcca cactctagct gtctcaggag tccccaaaga tctcaaagaa agtcacaggg    3240
gggggccagt cttaaaaacc tactcccgaa gcccagtcca cacaagtacc aggaacgtga    3300
gagcagcaaa agggtttata gggttccctc aagtaattcg gcaggaccaa gacactgatc    3360
atccggagaa tatggaagct tacgagacag tcagtgcatt tatcacgact gatctcaaga    3420
agtactgcct taattggaga tatgagacca tcagcttgtt tgcacagagg ctaaatgaga    3480
tttacggatt gccctcattt ttccagtggc tgcataagag gcttgagacc tctgtcctgt    3540
atgtaagtga ccctcattgc ccccccgacc ttgacgccca tcccgttta tataaagtcc    3600
ccaatgatca atcttcatt aagtacccta tgggaggtat agaagggtat tgtcagaagc    3660
tgtggaccat cagcaccatt ccctatctat acctggctgc ttatgagagc ggagtaagga    3720
ttgcttcgtt agtgcaaggg gacaatcaga ccatagccgt aacaaaaagg gtacccagca    3780
catggcccta caaccttaag aaacgggaag ctgctagagt aactagagat tactttgtaa    3840
ttcttaggca aaggctacat gatattggcc atcacctcaa ggcaaatgag acaattgttt    3900
catcacattt ttttgtctat tcaaaaggaa tatattatga tgggctactt gtgtcccaat    3960
cactcaagag catcgcaaga tgtgtattct ggtcagagac tatagttgat gaaacaaggg    4020
cagcatgcag taatattgct acaacaatgg ctaaaagcat cgagagaggt tatgaccgtt    4080
accttgcata ttccctgaac gtcctaaaag tgatacagca aattctgatc tctcttggct    4140
tcacaatcaa ttcaaccatg acccgggatg tagtcatacc cctcctcaca acaacgacc    4200
tcttaataag gatggcactg ttgcccgctc ctattggggg gatgaattat ctgaatatga    4260
gcaggctgtt tgtcagaaac atcggtgatc cagtaacatc atcaattgct gatctcaaga    4320
gaatgattct cgcctcacta atgcctgaag agaccctcca tcaagtaatg acacaacaac    4380
cgggggactc ttcattccta gactgggcta gcgacccta ctcagcaaat cttgtatgtg    4440
tccagagcat cactagactc ctcaagaaca taactgcaag gtttgtcctg atccatagtc    4500
caaacccaat gttaaaagga ttattccatg atgacagtaa agaagaggac gagggactgg    4560
cggcattcct catggacagg catattatag tacctagggc agctcatgaa atcctggatc    4620
atagtgtcac agggggcaaga gagtctattg caggcatgct ggataccaca aaaggcttga    4680
ttcgagccag catgaggaag gggggggttaa cctctcgagt gataaccaga ttgtccaatt    4740
atgactatga acaattcaga gcagggatgg tgctattgac aggaagaaag agaaatgtcc    4800
tcattgacaa agagtcatgt tcagtgcagc tggcgagagc tctaagaagc catatgtggg    4860
cgaggctagc tcgaggacgg cctatttacg gccttgaggt ccctgatgta ctagaatcta    4920
tgcgaggcca ccttattcgg cgtcatgaga catgtgtcat ctgcgagtgt ggatcagtca    4980
actacggatg gttttttgtc ccctcgggtt gccaactgga tgatattgac aaggaaacat    5040
catccttgag agtcccatat attggttcta ccactgatga gagaacagac atgaagcttg    5100
ccttcgtaag agcccccaagt cgatccttgc gatctgctgt tagaatagca acagtgtact    5160
catgggctta cggtgatgat gatagctctt ggaacgaagc ctggttgttg gctaggcaaa    5220
```

```
gggccaatgt gagcctggag gagctaaggg tgatcactcc catctcaact tcgactaatt    5280
tagcgcatag gttgagggat cgtagcactc aagtgaaata ctcaggtaca tcccttgtcc    5340
gagtggcgag gtataccaca atctccaacg acaatctctc atttgtcata tcagataaga    5400
aggttgatac taactttata taccaacaag gaatgcttct agggttgggt gttttagaaa    5460
cattgtttcg actcgagaaa gataccggat catctaacac ggtattacat cttcacgtcg    5520
aaacagattg ttgcgtgatc ccgatgatag atcatcccag gatacccagc tcccgcaagc    5580
tagagctgag ggcagagcta tgtaccaacc cattgatata tgataatgca cctttaattg    5640
acagagatgc aacaaggcta tacacccaga gccataggag gcaccttgtg gaatttgtta    5700
catggtccac accccaacta tatcacattt tagctaagtc cacagcacta tctatgattg    5760
acctggtaac aaaatttgag aaggaccata tgaatgaaat ttcagctctc ataggggatg    5820
acgatatcaa tagtttcata actgagtttc tgctcataga gccaagatta ttcactatct    5880
acttgggcca gtgtgcggcc atcaattggg catttgatgt acattatcat agaccatcag    5940
ggaaatatca gatgggtgag ctgttgtcat cgttcctttc tagaatgagc aaaggagtgt    6000
ttaaggtgct tgtcaatgct ctaagccacc caaagatcta caagaaattc tggcattgtg    6060
gtattataga gcctatccat ggtccttcac ttgatgctca aaacttgcac acaactgtgt    6120
gcaacatggt ttacacatgc tatatgacct acctcgacct gttgttgaat gaagagttag    6180
aagagttcac atttctcttg tgtgaaagcg acgaggatga agtaccggac agattcgaca    6240
acatccaggc aaaacactta tgtgttctgg cagatttgta ctgtcaacca gggacctgcc    6300
caccaattcg aggtctaaga ccggtagaga aatgtgcagt tctaaccgac catatcaagg    6360
cagaggctat gttatctcca gcaggatctt cgtggaacat aaatccaatt attgtagacc    6420
attactcatg ctctctgact tatctccggc gaggatcgat caaacagata agattgagag    6480
ttgatccagg attcattttc gacgccctcg ctgaggtaaa tgtcagtcag ccaaagatcg    6540
gcagcaacaa catctcaaat atgagcatca aggctttcag acccccacac gatgatgttg    6600
caaaattgct caaagatatc aacacaagca agcacaatct tcccatttca ggggcaatc    6660 tcgccaatta tgaaatccat gctttccgca gaatcgggtt gaactcatct gcttgctaca    6720
aagctgttga gatatcaaca ttaattagga gatgccttga gccaggggag gacggcttgt    6780
tcttgggtga gggatcgggt tctatgttga tcacttataa agagatactt aaactaaaca    6840
agtgcttcta taatagtggg gtttccgcca attctagatc tggtcaaagg gaattagcac    6900
cctatccctc cgaagttggc cttgtcgaac acagaatggg agtaggtaat attgtcaaag    6960
tgctctttaa cgggaggccc gaagtcacgt gggtaggcag tgtagattgc ttcaatttca    7020
tagttagtaa tatccctacc tctagtgtgg ggtttatcca ttcagatata gagaccttgc    7080
ctgacaaaga tactatagag aagctagagg aattggcagc catcttatcg atggctctgc    7140
tcctgggcaa aataggatca atactggtga ttaagcttat gccttcagc ggggattttg    7200 ttcagggatt tataagttat gtagggtctc attatagaga agtgaacctt gtataccct a   7260 gatacagcaa cttcatctct actgaatctt atttggttat gacagatctc aaggctaacc    7320
ggctaatgaa tcctgaaaag attaagcagc agataattga atcatctgtg aggacttcac    7380
ctggacttat aggtcacatc ctatccatta agcaactaag ctgcatacaa gcaattgtgg    7440
gagacgcagt tagtagaggt gatatcaatc ctactctgaa aaacttaca cctatagagc    7500 aggtgctgat caattgcggg ttggcaatta acggacctaa gctgtgcaaa gaattgatcc    7560
accatgatgt tgcctcaggg caagatggat tgcttaattc tatactcatc ctctacaggg    7620
```

```
agttggcaag attcaaagac aaccaaagaa gtcaacaagg gatgttccac gcttaccccg    7680
tattggtaag tagcaggcaa cgagaactta tatctaggat cacccgcaaa ttctgggggc    7740
acattcttct ttactccggg aacaaaaagt tgataaataa gtttatccag aatctcaagt    7800
ccggctatct gatactagac ttacaccaga atatcttcgt taagaatcta tccaagtcag    7860
agaaacagat tattatgacg gggggtttga aacgtgagtg ggttttttaag gtaacagtca    7920 aggagaccaa agaatggtat aagttagtcg gatacagtgc cctgattaag gactaattgg    7980
ttgaactccg gaaccctaat cctgccctag gtggttaggc attatttacc tcgaggggc    8040 cggatccact agttctagaa aaaaaaaaaa aaaaaaaaaa aaaaaaaaaa aaaaaaaaaa    8100
aaaaaaaaaa aaaaaaaaaa acgtcgcgca ggtgacaatg tcgagctagc tatgaattcc    8160
ccggggagct cactagtgga tccctgcagc tcgagaggcc taattaatta agtcgacgat    8220
ccggctgcta acaaagcccg aaaggaagct gagttggctg ctgccaccgc tgagcaataa    8280
ctagcataac cccttggggc ctctaaacgg gtcttgaggg gttttttgct gaaaggagga    8340
actatatccg gatcgagatc aattctgtga gcgtatggca aacgaaggaa aaatagttat    8400
agtagccgca ctcgatggga catttcaacg taaaccgttt aataatattt tgaatcttat    8460
tccattatct gaaatggtgg taaaactaac tgctgtgtgt atgaaatgct ttaaggaggc    8520
ttccttttct aaacgattgg gtgaggaaac cgagatagaa ataataggag gtaatgatat    8580
gtatcaatcg gtgtgtagaa agtgttacat cgactcataa tattatattt tttatctaaa    8640
aaactaaaaa taaacattga ttaaatttta atataatact taaaaatgga tgttgtgtcg    8700
ttagataaac cgtttatgta ttttgaggaa attgataatg agttagatta cgaaccagaa    8760
agtgcaaatg aggtcgcaaa aaaactgccg tatcaaggac agttaaaact attactagga    8820
gaattatttt ttcttagtaa gttacagcga cacggtatat tagatggtgc caccgtagtg    8880
tatataggat ctgctcccgg tacacatata cgttatttga gagatcattt ctataattta    8940
ggagtgatca tcaaatggat gctaattgac ggccgccatc atgatcctat tttaaatgga    9000
ttgcgtgatg tgactctagt gactcggttc gttgatgagg aatatctacg atccatcaaa    9060
aaacaactgc atccttctaa gattatttta atttctgatg tgagatccaa acgaggagga    9120
aatgaaccta gtacggcgga tttactaagt aattacgctc tacaaaatgt catgattagt    9180
attttaaacc ccgtggcgtc tagtcttaaa tggagatgcc cgtttccaga tcaatggatc    9240
aaggactttt atatcccaca cggtaataaa atgttacaac cttttgctcc ttcatattca    9300
gggccgtcgt tttacaacgt cgtgactggg aaaaccctgg cgttacccaa cttaatcgcc    9360
ttgcagcaca tccccctttc gccagctggc gtaatagcga agaggcccgc accgatcgcc    9420
cttcccaaca gttgcgcagc ctgaatgcg aatggcgcga cgcgccctgt agcggcgcat    9480
taagcgcggc gggtgtggtg gttacgcgca gcgtgaccgc tacacttgcc agcgccctag    9540
cgcccgctcc tttcgctttc ttcccttcct ttctcgccac gttcgccggc tttccccgtc    9600
aagctctaaa tcggggctc cctttagggt tccgatttag tgctttacgg cacctcgacc    9660
ccaaaaaact tgattagggt gatggttcac gtagtgggcc atcgccctga tagacgtttt    9720
ttcgcccttt gacgttggag tccacgttct ttaatagtgg actcttgttc caaactggaa    9780
caacactcaa ccctatctcg gtctattctt ttgatttata agggattttg ccgatttcgg    9840
cctattggtt aaaaaatgag ctgatttaac aaaaatttaa cgcgaatttt aacaaaatat    9900
taacgtttac aatttcccag gtggcacttt tcggggaaat gtgcgcggaa ccctatttg    9960
```

-continued

```
tttattttc  taaatacatt  caaatatgta  tccgctcatg  agacaataac  cctgataaat    10020
gcttcaataa  tattgaaaaa  ggaagagtat  gagtattcaa  catttccgtg  tcgcccttat    10080
tccctttttt  gcggcatttt  gccttcctgt  ttttgctcac  ccagaaacgc  tggtgaaagt    10140
aaaagatgct  gaagatcagt  tgggtgcacg  agtgggttac  atcgaactgg  atctcaacag    10200
cggtaagatc  cttgagagtt  ttcgccccga  agaacgtttt  ccaatgatga  gcacttttaa    10260
agttctgcta  tgtggcgcgg  tattatcccg  tattgacgcc  gggcaagagc  aactcggtcg    10320
ccgcatacac  tattctcaga  atgacttggt  tgagtactca  ccagtcacag  aaaagcatct    10380
tacggatggc  atgacagtaa  gagaattatg  cagtgctgcc  ataaccatga  gtgataacac    10440
tgcggccaac  ttacttctga  caacgatcgg  aggaccgaag  gagctaaccg  cttttttgca    10500
caacatgggg  gatcatgtaa  ctcgccttga  tcgttgggaa  ccggagctga  atgaagccat    10560
accaaacgac  gagcgtgaca  ccacgatgcc  tgtagcaatg  gcaacaacgt  tgcgcaaact    10620
attaactggc  gaactactta  ctctagcttc  ccggcaacaa  ttaatagact  ggatggaggc    10680
ggataaagtt  gcaggaccac  ttctgcgctc  ggcccttccg  gctggctggt  ttattgctga    10740
taaatctgga  gccggtgagc  gtgggtctcg  cggtatcatt  gcagcactgg  ggccagatgg    10800
taagccctcc  cgtatcgtag  ttatctacac  gacggggagt  caggcaacta  tggatgaacg    10860
aaatagacag  atcgctgaga  taggtgcctc  actgattaag  cattggtaac  tgtcagacca    10920
agtttactca  tatatacttt  agattgattt  aaaacttcat  ttttaattta  aaaggatcta    10980
ggtgaagatc  cttttgata  atctcatgac  caaaatccct  taacgtgagt  tttcgttcca    11040
ctgagcgtca  gaccccgtag  aaaagatcaa  aggatcttct  tgagatcctt  ttttctgcg    11100
cgtaatctgc  tgcttgcaaa  caaaaaaacc  accgctacca  gcggtggttt  gtttgccgga    11160
tcaagagcta  ccaactcttt  ttccgaaggt  aactggcttc  agcagagcgc  agataccaaa    11220
tactgtcctt  ctagtgtagc  cgtagttagg  ccaccacttc  aagaactctg  tagcaccgcc    11280
tacatacctc  gctctgctaa  tcctgttacc  agtggctgct  gccagtggcg  ataagtcgtg    11340
tcttaccggg  ttggactcaa  gacgatagtt  accggataag  gcgcagcggt  cgggctgaac    11400
ggggggttcg  tgcacacagc  ccagcttgga  gcgaacgacc  tacaccgaac  tgagatacct    11460
acagcgtgag  ctatgagaaa  gcgccacgct  tcccgaaggg  agaaaggcgg  acaggtatcc    11520
ggtaagcggc  agggtcggaa  caggagagcg  cacgagggag  cttccagggg  gaaacgcctg    11580
gtatctttat  agtcctgtcg  ggtttcgcca  cctctgactt  gagcgtcgat  ttttgtgatg    11640
ctcgtcaggg  gggcggagcc  tatggaaaaa  cgccagcaac  gcggcctttt  tacggttcct    11700
ggccttttgc  tggccttttg  ctcacatgtt  ctttcctgcg  ttatcccctg  attctgtgga    11760
taaccgtatt  accgcctttg  agtgagctga  taccgctcgc  cgcagccgaa  cgaccgagcg    11820
cagcgagtca  gtgagcgagg  aagcggaaga  gcgcccaata  cgcaaaccgc  ctctccccgc    11880
gcgttggccg  attcattaat  gcagctggca  cgacaggttt  cccgactgga  aagcgggcag    11940
tgagcgcaac  gcaattaatg  tgagttagct  cactcattag  gcaccccagg  ctttacactt    12000
tatgcttccg  gctcgtatgt  tgtgtggaat  tgtgagcgga  taacaatttc  acacaggaaa    12060
cagctatgac  catgattacg  cc                                                12082
```

<210> SEQ ID NO 3
<211> LENGTH: 32
<212> TYPE: DNA
<213> ORGANISM: Artificial sequence
<220> FEATURE:
<223> OTHER INFORMATION: Primer -continued

<400> SEQUENCE: 3
atctggcacc acaccttcta caatgagctg cg                              32

<210> SEQ ID NO 4
<211> LENGTH: 32
<212> TYPE: DNA
<213> ORGANISM: Artificial sequence
<220> FEATURE:
<223> OTHER INFORMATION: Primer

<400> SEQUENCE: 4
cgtcatactc ctgcttgctg atccacatct gc                              32

<210> SEQ ID NO 5
<211> LENGTH: 25
<212> TYPE: DNA
<213> ORGANISM: Artificial sequence
<220> FEATURE:
<223> OTHER INFORMATION: Primer

<400> SEQUENCE: 5
attgggtctg ggaacatttc tcttc                                      25

<210> SEQ ID NO 6
<211> LENGTH: 25
<212> TYPE: DNA
<213> ORGANISM: Artificial sequence
<220> FEATURE:
<223> OTHER INFORMATION: Primer

<400> SEQUENCE: 6
gtgagattta aacattcctc ttcgg                                      25

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
gagcaacttc tttcaaccac                                            20

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
gaacaccagc atcttctcca                                            20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
gaacgattcc atcactatcc                                            20

<210> SEQ ID NO 10

```
<211> LENGTH: 20
<212> TYPE: DNA
<213> ORGANISM: Artificial sequence
<220> FEATURE:
<223> OTHER INFORMATION: Primer

<400> SEQUENCE: 10
ggcatcatta tatttccgca                                             20

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
cttctcagca gatacatcag                                             20

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
gttacaagtc caaagtctcc                                             20

<210> SEQ ID NO 13
<211> LENGTH: 9
<212> TYPE: PRT
<213> ORGANISM: Artificial sequence
<220> FEATURE:
<223> OTHER INFORMATION: MSLN 531-539 epitope

<400> SEQUENCE: 13

Val Leu Pro Leu Thr Val Ala Glu Val
1               5

<210> SEQ ID NO 14
<211> LENGTH: 10
<212> TYPE: PRT
<213> ORGANISM: Artificial sequence
<220> FEATURE:
<223> OTHER INFORMATION: MSLN 541-550 epitope

<400> SEQUENCE: 14

Lys Leu Leu Gly Pro His Val Glu Gly Leu
1               5                   10
```